US005801201A

United States Patent [19]
Graudums et al.

[11] Patent Number: 5,801,201
[45] Date of Patent: Sep. 1, 1998

[54] 1-PHENYL-2-DIMENTHYLAMINOMETHYL-CYCLOHEXAN-1-OL COMPOUNDS AS PHARMACEUTICAL ACTIVE INGREDIENTS

[75] Inventors: Ivars Graudums, Stolberg; Werner Winter, Aachen; Ernst Frankus, Stolberg; Wolfgagn Werner Alfred Strassburger, Wuerselen; Elmar Josef Friderichs, Stolberg, all of Germany

[73] Assignee: Gruenenthal GmbH, Aachen, Germany

[21] Appl. No.: 769,744

[22] Filed: Dec. 19, 1996

[30] Foreign Application Priority Data

Dec. 20, 1995 [DE] Germany ............. 195 47 766.9

[51] Int. Cl.$^6$ ............. A61K 31/135; C07K 217/56
[52] U.S. Cl. ............. 514/646; 514/647; 564/440; 564/442; 564/443
[58] Field of Search ............. 564/440, 442, 564/443; 514/646, 647

[56] References Cited

U.S. PATENT DOCUMENTS 3,652,589 3/1972 Flick et al. ............. 548/578

FOREIGN PATENT DOCUMENTS 616646 4/1962 Belgium .
997399 4/1964 United Kingdom .

OTHER PUBLICATIONS

Sawa, Yoichi et al., "1-Substituted 2-(dimethylaminomethyl)-5,5-dimethyl-1-cyclohexanols", *Chemical Abstracts*, vol. 87, No. 7, Aug. 15, 1977.

Kato, Takeshi et al., "Synthesis of N-substituted (6-benzyl-4,4-dimethyl-2-cyclohexenyl) methylamines and related compounds", *Chemical Abstracts*, vol. 101, No. 3, Jul. 16, 1984.

Reichert et al., "Aminomethylierungsprodukte alkulsubstituierter Cyclohexanone", *Arzneimittel-Forsch.*, No. 13, pp. 991–999 (1963).

Krapcho et al., "Solvolysis Studies of Cycloalkylcarbinyl Tosylates . . . ", *Journal of Organic Chemistry*, vol. 36, No. 1, pp. 146–157, 1971.

Shiotani et al., "Studies on Structure–Activity Relationship of Analgetics. XIII Syntheses of Homobenzomporhans and Related Compounds", *Chem. Pharm. Bull.*, vol. 20, pp. 277–283, 1972.

Hwu Jr., et al., "Total Synthesis of (+/−)Androst-4-en-3-one-carboxylic Acid", *J. Chem. Soc., Chem. Commun.*, pp. 721–723 (1984).

Gray et al., "Mass Spectrometry in Structural and Stereochemical Problems. CLXXXI. Further Studies of Remote Group Interactions after Electron Impact in 4-Substituted Cyclohexanones", *Journal of Organic Chemistry*, vol. 35, No. 5, May 1970.

Goodman and Gilman, Chapters 21 and 22, *The Pharmacological Basis of Therapeutics*, Pergamon Press, New York, 1990, pp. 485–573.

Raviña et al., "Derivados Del Ciclohexano 4,4-Disustituido", Anales de Quimica, vol. 69, pp. 915–920 (1973).

Raffa et al., "Complementary and Synergistic Antinociceptive Interaction between the Enantiomers of Tramadol", *J. Pharmacol. Exp. Ther.*, vol. 267, No. 1, p. 340 (1993).

Raffa et al., "Opioid and Nonopioid Components Independently Contribute to the Mechanism of Action of Tramadol, and Atypical Opioid Analgesic", *J. Pharmacol. Exp. Ther.*, vol. 260, No. 1, pp. 275–285 (1992).

Litchfield et al., "A Simplified Method of Evaluating Dose-Effect Experiments", *J. Pharmacol. Exp. Ther.*, vol. 96, pp. 99–113 (1949).

D'Amour et al., "A Method for Determining Loss of Pain Sensation", *J. Pharmacol. Exp. Ther.*, vol. 72, pp. 74–79 (1941).

*Primary Examiner*—Richard L. Raymond
*Attorney, Agent, or Firm*—Evenson, McKeown, Edwards & Lenahan, PLLC

[57] ABSTRACT

1-phenyl-2-dimethylaminomethyl-cyclohexan-1-ol compounds, methods of preparing them and the use of these compounds in drugs are described.

8 Claims, No Drawings

1-PHENYL-2-DIMENTHYLAMINOMETHYL-CYCLOHEXAN-1-OL COMPOUNDS AS PHARMACEUTICAL ACTIVE INGREDIENTS

This invention relates to 1-phenyl-2-dimethylaminomethyl-cyclohexan-1-ol compounds, to methods of preparing them and to the use of these compounds in drugs.

The treatment of chronic and non-chronic pain conditions is of great importance in medicine. There is currently a world-wide need for additional pain therapy which is not exclusively opioid but which exhibits good efficacy. The pressing requirement for a target-oriented treatment of chronic and non-chronic pain conditions which is right for the patient, which is to be understood as the successful and satisfactory treatment of pain for the patients, is documented in the large number of scientific works which have recently appeared in the field of applied analgesics or on basic research on nociception.

Opioids have been used for many years for the treatment of pain, even though they give rise to a series of side effects, for example dependency, respiratory depression, gastrointestinal inhibition effects and obstipation. Special precautions, for example special prescription regulations, are therefore necessary in order to administer opioids over an extended period of time or in high dosages (Goodman, Gilman "The Pharmaceutical Basis of Therapeutics" Pergamon Press, New York, 1990).

Tramadol hydrochloride—(1RS,2RS)-2-dimethylaminomethyl-1-(3-methoxyphenyl)-cyclohexanol hydrochloride—assumes a special position amongst centrally acting analgesics, since this active ingredient acts as a strong inhibitor of pain without the side effects which are known for opioids (J. Pharmacol. Exp. Ther. 267, 331 (1993)). Tramadol is a racemate and consists of equal amounts of (+) and (−) enantiomers. In vivo, this active ingredient forms the metabolite o-desmethyl-tramadol, which likewise exists as a mixture of enantiomers. Investigations have shown that both the enantiomers of tramadol and the enantiomers of the tramadol metabolite are involved in the analgesic effect (J. Pharmacol. Exp. Ther. 260, 275 (1992)).

1,2,4,4-tetrasubstituted cyclohexanol compounds which are used as spasmolytics are known from An. Quim., 69 (7–8), 915–920 (1973).

Belgian Patent Specification BE 616,646 describes 1,2,4,4-tetrasubstituted cyclohexanol compounds with an antitussive effect.

1,2,4-trisubstituted cyclohexanol compounds are disclosed in Arzneimittel-Forsch. 13, 991–999 (1963). Some of these compounds have a spasmolytic effect.

The underlying object of the present invention was to develop substances with an analgesic effect which are suitable for the treatment of severe pain without giving rise to the side effects which are typical of opioids. The object was also that the substances to be developed should not exhibit the side effects which occur in some cases during treatment with tramadol, for example nausea and vomiting.

It has now been found that the requirements imposed on the substances to be developed are fulfilled by certain 1-phenyl-2-dimethylaminomethyl-cyclohexan-1-ol compounds. These compounds are distinguished by an analgesic effect which is significantly increased compared with tramadol. They can thus be used even in cases of particularly severe pain in which an opioid effect of medium strength is no longer sufficient. The compounds can therefore be administered in smaller doses, which enables non-specific side effects to be reduced. Moreover, due to their stronger analgesic effect other areas of application, which are not covered by the medium strength opioid effect of tramadol, can be opened up in the field of analgesics, for example balanced narcosis or severe or very severe pain conditions in the perioperative field.

Accordingly, the present invention relates to 1-phenyl-2-dimethylaminomethyl-cyclohexan-1-ol compounds of formula I

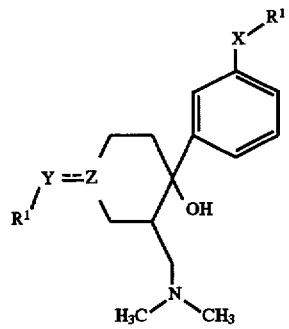

in which X represents O or S, $R^1$ represents H, $C_{1-6}$ alkyl, $C_{2-6}$ alkenyl, $C_{5-7}$ cycloalkyl or halogenated $C_{1-6}$ alkyl, the

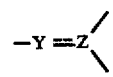

grouping represents

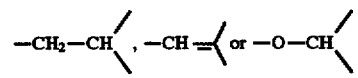

$R^2$ represents $C_{1-6}$ alkyl, $C_{2-6}$ alkenyl, $C_{5-7}$ cycloalkylmethyl substituted or unsubstituted phenyl or substituted or unsubstituted benzyl, in the form of their bases or salts of physiologically compatible acids.

Preferred 1-phenyl-2-dimethylaminomethyl-cyclohexan-1-ols consist of compounds of formula I in which $R^1$ represents H, $C_{1-4}$ alkyl, 2'-methyl-2'-propenyl, cyclopentyl or fluoroethyl, with the proviso that $R^1$ is $C_{1-4}$ alkyl when X represents S, and $R^2$ represents $C_{1-4}$ alkyl, $C_{2-4}$ alkenyl, cyclopentylmethyl, phenyl, $C_{1-4}$ alkoxyphenyl, benzyl, $C_{1-4}$ alkylbenzyl, singly or doubly halogenated phenyl or singly or doubly halogenated benzyl.

Compounds of formula I in which $R^1$ represents H, methyl, ethyl, isopropyl, 2'-methyl-2'-propenyl, cyclopentyl or fluoroethyl, with the proviso that $R^1$ is methyl when X represents S, and $R^2$ represents methyl, propyl, 2'-methyl-propyl, allyl, 2'-methyl-2'-propenyl, cyclopentylmethyl, phenyl, 3-methoxyphenyl, benzyl, 4-tert-butylbenzyl, 4-chlorobenzyl, 4-fluorobenzyl or 3,4-dichlorobenzyl, are particularly preferred 1-phenyl-2-dimethylaminomethyl-cyclohexan-1-ol compounds.

Compounds which are most particularly preferred are 1-phenyl-2-dimethylaminomethyl-cyclohexan-1-ols of formula I in which $R^1$ represents H, methyl or cyclopentyl, with the proviso that $R^1$ is methyl when X represents S, the

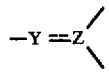

grouping represents

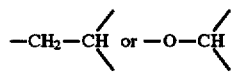

and $R^2$ represents cyclopentylmethyl, benzyl and 4-chlorophenyl.

Selected 1-phenyl-2-dimethylaminomethyl-cyclohexan-1-ol compounds are compounds of formula I in which X is O, $R^1$ represents H or methyl, the

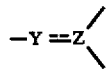

grouping represents

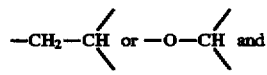

$R^2$ is benzyl.

1-phenyl-2-dimethylaminomethyl-cyclohexan-1-ol compounds in the form of their diastereoisomers preferably have the configuration of formula Ia

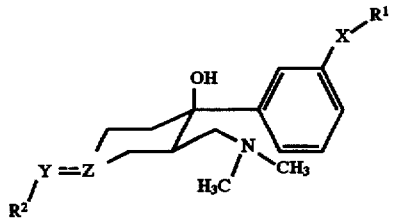

in which the phenyl ring and the dimethylaminomethyl group are situated trans in relation to each other.

The present invention also relates to a method of preparing a 1-phenyl-2-dimethylaminomethyl-cyclohexan-1-ol compound of formula I, in which X represents O or S, $R^1$ represents $C_{1-6}$ alkyl, $C_{2-6}$ alkenyl, $C_{5-7}$ cycloalkyl, halogenated $C_{1-6}$ alkyl, benzyl, diarylalkylsilyl or trialkylsilyl, the

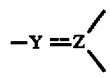

grouping is

and $R^2$ represents $C_{1-6}$ alkyl, $C_{2-6}$ alkenyl, $C_{5-7}$ cycloalkylmethyl, substituted or unsubstituted phenyl or substituted or unsubstituted benzyl, which is characterised in that a 4-substituted cyclohexan-1-one of formula IIa

is prepared either by alkylating a compound of formula IV

in which A is a branched or unbranched $C_nH_{2n}$ radical and n represents an integer between 2 and 6, with a compound of formula III $R^2$—G in which G is Cl, Br, I or toluenesulphonyloxy, and subsequently deacetylating it by means of proton catalysis, or by alkylating a compound of formula V

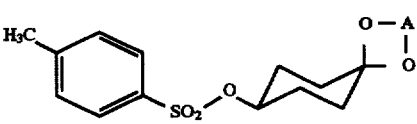

with an alcoholate which is prepared from an alcohol of formula VI $R^2$—OH, and subsequently deacetylating it by means of proton catalysis to form a compound of formula IIa, reacting the compound of formula IIa which is obtained, either with dimethylamine in a Mannich reaction or with dimethylammonium methylene chloride, to form a compound of formula VIIa

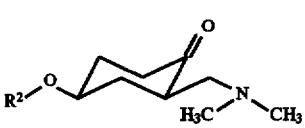

which is converted into a compound of formula I with an organometallic compound of formula VIII

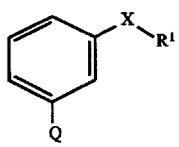

in which Q represents MgCl, MgBr, MgI or Li.

The reaction of a compound of formula IV with a compound of formula III is carried out by introducing a hydride such as NaH or an alcoholate such as potassium tert.-butylate into an inert, polar solvent, e.g. dimethylformamide, subsequently adding a compound of formula IV, and stirring at temperatures between 20° C. and 60° C. A compound of formula III is then added and is alkylated at temperatures between 20° C. and 120° C. In order to prepare the ketone IIa the alkylated compound IV is dissolved in an ether, for example diethyl ether, diisopropyl ether, tetrahydrofuran or dioxan, or in a hydrocarbon, and is deacetylated by stirring with acids such as HCl, HBr or $H_2SO_4$ (Gray et al., J. Org. Chem. 35 (1970), 1525; Krepcho et al., J. Org. Chem. 36 (1971), 146).

A further possible route for preparing a ketone of formula IIa consists of the alkylation of an alcoholate derived from an alcohol of formula VI in a polar, inert solvent, for example dimethylformamide, with a compound of formula V, and subsequent deacetylation. Deacetylation is likewise effected under the aforementioned conditions. The alcoholate of an alcohol of formula VI is obtained by reaction with NaH, an alcoholate, NaOH or KOH, for example.

A Mannich reaction with dimethylamine can be performed with a compound of formula IIa at temperatures between 40° C. and 120° C., whereupon a compound of formula VIIa is produced. Straight chain or branched $C_{1-4}$ alcohols or acetic acid are employed as solvents. Formaldehyde can be used as a formalin solution or as paraformaldehyde (J. R. Hwu et al., J. Chem. Soc., Chem. Commun. 1984, 721).

A ketone of formula VIIa can also be obtained in the form of its hydrochloride by the reaction of a ketone of formula IIa with dimethylammonium methylene chloride in aprotic solvents, for example acetonitrile, at temperatures between 20° C. and 40° C.

The reaction of a ketone of formula VIIa with a Grignard compound of formula VIII or with an organolithium compound of formula VIII can be conducted in aliphatic ethers, for example diethyl ether and/or tetrahydrofuran, at a temperature between 30° C. and 80° C. Organolithium compounds of formula VIII which can be used for the present reaction can be obtained by the reaction of a compound of formula VIII, in which Q represents Cl, Br or I, with an n-butyllithium/hexane solution, for example, by halogen/lithium exchange.

The present invention also relates to a method of preparing a 1-phenyl-2-dimethylaminomethyl-cyclohexan-1-ol compound of formula I, in which X represents O or S, $R^1$ represents $C_{1-6}$ alkyl, $C_{2-6}$ alkenyl, $C_{5-7}$ cycloalkyl, halogenated $C_{1-6}$ alkyl, benzyl, diarylalkylsilyl or trialkylsilyl, the

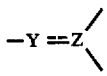

grouping is

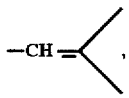

and $R^2$ represents $C_{1-6}$ alkyl, $C_{2-6}$ alkenyl, $C_{5-7}$ cycloalkylmethyl, substituted or unsubstituted phenyl or substituted or unsubstituted benzyl,
which is characterised in that a 4-substituted cyclohexan-1-one of formula IIb

is prepared, either by reacting a Grignard compound of formula IX $R^2$—$CH_2$—Mg—Hal, in which Hal represents Cl, Br or I, with a ketone of formula X

in which A is a branched or unbranched $C_nH_{2n}$ radical where n is an integer between 2 and 6,
to form a compound of formula XI

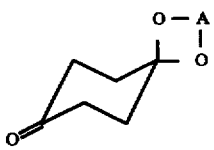

from which a keto compound of formula XII

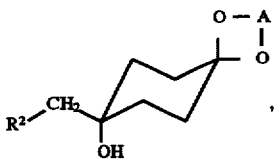

is subsequently prepared by means of proton-catalysed deacetylation, and the compound of formula IIb is obtained by subsequent dehydration, or a ketone of formula X is subjected to a Wittig reaction with a phosphorane of formula XIII $R_3P$=$CH$—$R^2$, in which R represents aryl, to form a compound of formula XIV

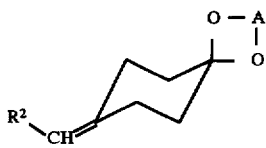

which is subsequently converted by means of proton catalysis into a ketone of formula IIb, and thereafter the compound of formula IIb which is obtained is reacted, either with dimethylamine in a Mannich reaction or with dimethylammonium methylene chloride, to form a compound of formula VIIb

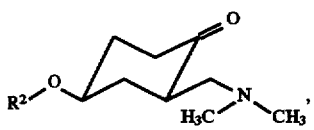

which is converted into a compound of formula I with an organometallic compound of formula VIII, in which Q represents MgCl, MgBr, MgI or Li.

The present invention further relates to a method of preparing a 1-phenyl-2-dimethylaminomethyl-cyclohexan-1-ol compound of formula I, in which X represents O or S, R$^1$ represents C$_{1-6}$ alkyl, C$_{2-6}$ alkenyl, C$_{5-7}$ cycloalkyl, halogenated C$_{1-6}$ alkyl, benzyl, diarylalkylsilyl or trialkylsilyl, the

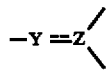

grouping is

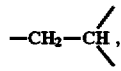

and R$^2$ represents C$_{1-6}$ alkyl, C$_{2-6}$ alkenyl, C$_{5-7}$ cycloalkylmethyl, substituted or unsubstituted phenyl or substituted or unsubstituted benzyl, which is characterised in that a compound of formula IIb, which is prepared analogously to the method described above, is hydrogenated in the presence of a Pd or Pt catalyst to form a 4-substituted cyclohexan-1-one of formula IIc

the compound of formula IIc which is obtained is reacted, either with dimethylamine in a Mannich reaction or with dimethylammonium methylene chloride, to form a compound of formula VIIc

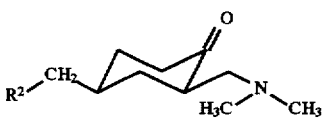

which is converted into a compound of formula I with an organometallic compound of formula VIII, in which Q represents MgCl, MgBr, MgI or Li.

A compound of formula XI can be prepared by the reaction of a compound of formula IX with a compound of formula X in aliphatic or cyclic ethers, for example diethyl ether or tetrahydrofuran, at temperatures between 30° C. and 100° C. In order to increase the yield of compound XI, 1,2-dibromoethane may be added, for example. The corresponding compound of formula XII is then obtained by splitting off the acetal group from the compound of formula XI. The compound of formula XII is reacted with formic acid, acetic anhydride or an inorganic acid chloride at temperatures between 20° C. and 120° C. to form a mixture of olefines. Compound IIb can be isolated from the mixture of olefines by known separation methods, for example by means of column chromatography.

If desired, the entire mixture of olefines can be hydrogenated in the presence of a Pt or Pd catalyst in acetic acid or in a straight chain or branched C$_{1-4}$ alcohol at 1-100 atm and temperatures between 20° C. and 100° C. to form a compound of formula IIc (Shiotani et al., Chem. Pharm. Bull., 20 (1972), 277).

A further possible route for obtaining a compound of formula IIb or IIc consists of the Wittig reaction of a ketone of formula X with a phosphorane of formula XIII, in which R is aryl, for example phenyl, to form a compound of formula XIV. The reaction is usually conducted in a cyclic ether, for example tetrahydrofuran, or in a hydrocarbon, for example toluene, at temperatures between 50° C. and 110° C. The compound of formula XIV which is obtained is deacetylated and dehydrated as described above. If desired, the compound of formula IIb which is obtained can be hydrogenated to form a compound of formula IIc.

The present invention also relates to a method of preparing a 1-phenyl-2-dimethylaminomethyl-cyclohexan-1-ol compound of formula I in which X represents O or S, R$^1$ represents H, the

grouping represents

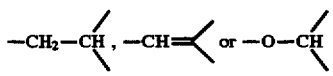

R$^2$ represents C$_{1-6}$ alkyl, C$_{2-6}$ alkenyl, C$_{5-7}$ cycloalkylmethyl, substituted or unsubstituted phenyl or substituted or unsubstituted benzyl, wherein the method is characterised in that either a compound of formula I, in which R$^1$ represents methyl, is reacted with diisobutylaluminium hydride, or a compound of formula I, in which R$^1$ is benzyl, is hydrogenated in the presence of a Pt or Pd catalyst, or a compound of formula I, in which R$^1$ represents diarylalkylsilyl or trialkylsilyl, is hydrolysed or reacted with tetra-n-butylammonium fluoride.

The reaction of a compound of formula I, in which $R^1$ is methyl and X is O, with diisobutylaluminium hydride, is preferably conducted in aromatic solvents, for example toluene, at temperatures between 60° C. and 130° C.

The hydrogenation of a compound of formula I, in which $R^1$ is benzyl and X is O, is usually conducted in the presence of a Pt or Pd catalyst in acetic acid or in a branched or unbranched $C_{1-4}$ alcohol at 1–100 atm and temperatures between 20° C. and 50° C.

If a compound of formula I, in which $R^1$ is a diarylalkylsilyl or trialkylsilyl radical, preferably tert.-butyldimethylsilyl or tert.-butyldiphenylsilyl, is present as a starting compound, the silyl group is split off with acids, for example dilute hydrochloric acid, or with tetra-n-butylammonium fluoride.

The present invention further relates to a method of preparing a 1-phenyl-2-dimethylaminomethyl-cyclohexan-1-ol compound of formula I, in which X represents O or S, $R^1$ represents H, $C_{1-6}$ alkyl, $C_{2-6}$ alkenyl, $C_{5-7}$ cycloalkyl, halogenated $C_{1-6}$ alkyl, benzyl, diarylalkylsilyl or triarylalkylsilyl, the

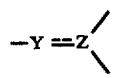

grouping represents

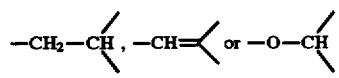

$R^2$ represents $C_{1-6}$ alkyl, $C_{2-6}$ alkenyl, $C_{5-7}$ cycloalkylmethyl, substituted or unsubstituted phenyl or substituted or unsubstituted benzyl, which is characterised in that a ketone of formula XV

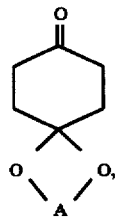

in which A is a branched or unbranched $C_nH_{2n}$ radical, where n is an integer between 2 and 6, is reacted with dimethylammonium methylene chloride to form a β-dimethylaminoketone of formula XVI

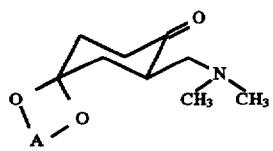

from which a compound of formula XVII

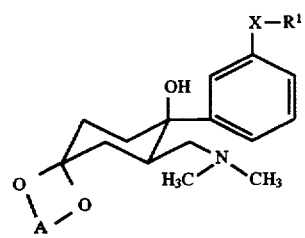

is subsequently prepared with an organometallic compound of formula VIII, in which Q represents MgCl, MgBr, MgI or Li, which compound of formula XVII is subsequently deacetylated by means of proton catalysis to form a compound of formula XVIII

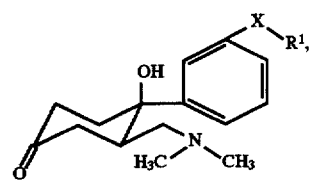

the compound of formula XVIII which is obtained is either reduced to form a 4-hydroxy derivative of formula XIX

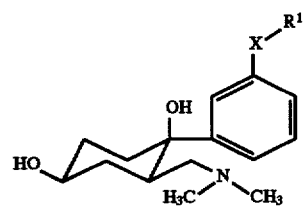

from which a compound of formula I is prepared, in which the

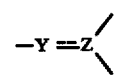

grouping is

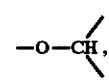

by subsequent alcoholate formation and reaction with a compound of formula III, in which G is Cl, Br, I or toluenesulphonyloxy, or the compound of formula XVIII which is obtained is reacted with a compound of formula XX

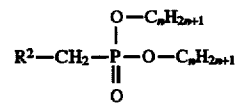

in which n represents an integer from 1–3, to form a compound of formula I, in which the

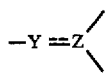

grouping is

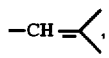

which is hydrogenated if desired to form a compound of formula I in which the

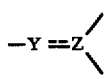

grouping is

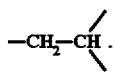

The reaction of the keto compound XV with dimethylmethylene ammonium chloride to form a β-dimethylaminoketone with a spirocyclic acetal structure of formula XVI is usually conducted in acetonitrile with acetyl chloride catalysis. The compound of formula XVI which is obtained is subsequently reacted with an organometallic compound of formula VIII in aliphatic or cyclic ethers, for example diethyl ether or tetrahydrofuran, at temperatures between 30° C. and 80° C., to form a compound of formula XVII. 1,2-dibromoethane can be added, for example, in order to increase the yield of compound XVII.

The compound of formula XVII which is obtained is dissolved in an ether, e.g. diethyl ether, diisopropyl ether, tetrahydrofuran or dioxan, or in a hydrocarbon. The spirocyclic acetal group is subsequently split off by stirring with acids, for example HCl, HBr or $H_2SO_4$, and a compound of formula XVIII is obtained. The subsequent reduction of the compound of formula XVIII to form a 4-hydroxy derivative of formula XIX can be effected with a complex alkali metal hydride, preferably sodium borohydride or lithium aluminium hydride, in an organic solvent, for example tetrahydrofuran, diethyl ether and/or a $C_{2-4}$ alcohol.

From the 4-hydroxy derivative of formula XIX which is obtained, the 4-alcoholate of compound XIX can be prepared with an alkali hydride, for example sodium hydride, in an aprotic solvent, e.g. diethyl ether, and is converted, in a subsequent reaction with a compound of formula III at temperatures between 40° C. and 100° C., to a compound of formula I, in which the

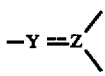

grouping is

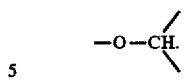

A further possible route for obtaining a compound of formula I, in which the

grouping is

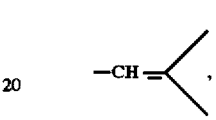

from a compound of formula XIX, consists of conducting a Horner-Emmons reaction with a compound of formula XX, in which n preferably represents 2, in a solvent, for example dimethylformamide, at temperatures between 0° C. and 20° C.

If desired, a subsequent hydrogenation reaction of a compound of formula I, in which the

grouping is

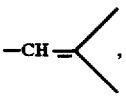

to form a compound of formula I, in which the

grouping is

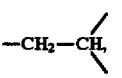

is conducted in the presence of a Pt or Pd catalyst in acetic acid or in a straight chain or branched $C_{1-4}$ alcohol at 1–100 atm and temperatures between 20° C. and 100° C.

The compounds of formula I according to the invention exist as diastereoisomers, enantiomers or racemates. The preparation of pure optical antipodes from a racemate is effected by methods which are known in the art.

The compounds according to the invention can be converted with physiologically compatible acids, for example hydrochloric acid, hydrobromic acid, sulphuric acid, methanesulphonic acid, formic acid, acetic acid, oxalic acid, succinic acid, tartaric acid. mandelic acid, fumaric acid, lactic acid, citric acid, glutamic acid and/or aspartic acid, into the salts thereof in the manner known in the art. Salt formation is preferably conducted in a solvent, for example diethyl ether, diisopropyl ether, an acetic acid alkyl ester, acetone and/or 2-butanone. Trimethylchlorosilane in the presence of water in one of the aforementioned solvents is also suitable for the preparation of the hydrochlorides.

The compounds according to the invention have a pronounced analgesic effect and are toxicologically harmless. They are therefore suitable as pharmaceutical active ingredients. Accordingly, the present invention also relates to the use of 1-phenyl-2-dimethylaminomethyl-cyclohexan-1-ol compounds of formula I as an active ingredient in drugs, preferably as an active ingredient in pain-killing drugs.

In addition to at least one 1-phenyl-2-dimethylaminomethyl-cyclohexan-1-ol compound of formula I, drugs according to the invention contain support materials, fillers, solvents, diluents, colorants and/or binders. The selection of the auxiliary materials and of the amounts to be used depends upon whether the drug is to be applied orally, intravenously, intraperitoneally, intradermally, intramuscularly, intranasally, buccally or locally, for example for infections of the skin, of the mucous membranes and of the eyes. Preparations in the form of tablets, dragees, capsules, granules, drops, juices and syrups are suitable for oral application. Solutions, suspensions, readily reconstitutable dry preparations and sprays are suitable for parenteral or topical application or for application by inhalation. Compounds according to the invention as a deposit in a dissolved form or in a patch, optionally with the addition of agents which promote dermal penetration, are examples of suitable percutaneous forms of application. The compounds according to the invention can be released in a delayed manner from forms of preparations which can be applied orally or percutaneously.

Intravenous administration of the drugs according to the invention is the preferred form of application.

The amount of active ingredient to be administered to the patient varies depending on the weight of the patient, on the type of application, on the indication and on the degree of severity of the illness. Doses within the range from 1 to 200 mg of at least one 1-phenyl-2-dimethylaminomethyl-cyclohexan-1-ol compound of formula I are usually applied.

EXAMPLES

Petroleum ether with a boiling range of 50°–70° C. was used unless indicated otherwise. The term "ether" denotes diethyl ether.

Silica gel 60 (0.040–0.063 mm) supplied by E. Merck, Darmstadt, was used as the stationary phase for column chromatography.

The mixture ratios of the elution media for the chromatographic methods are always given in volume/volume.

Racemate separations were performed on a Chiracel OD column supplied by Daicel Chemical Industries, Ltd.

m.p. denotes melting point, decompn. denotes decomposition and Ex. denotes Example.

Example 1

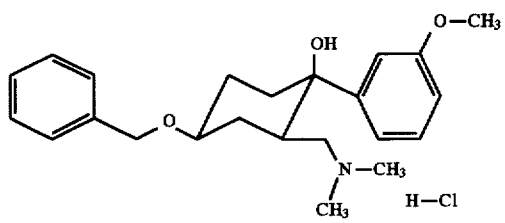

(1RS,2RS,4SR)-4-benzyloxy-2-dimethylaminomethyl-1-(3-methoxy-phenyl)-cyclohexanol hydrochloride (1)

2.42 g magnesium turnings (100 mmole) were stirred in 25 ml tetrahydrofuran, and 12.7 ml (100 mmole) 1-bromo-3-methoxybenzene, dissolved in 64 ml tetrahydrofuran, were added drop-wise. The mixture was boiled for 1 hour under reflux and then cooled to 5° C.–10° C. 13 g (50 mmole) 4-benzyloxy-2-dimethylaminomethyl-cyclohexanone, dissolved in 65 ml tetrahydrofuran, were then added drop-wise at this temperature (J. R. Hwu et al., J. Chem. Soc., Chem. Commun., 1984, 721–723). The mixture was stirred for 1 hour at room temperature, cooled to 5° C.–10° C., and the Grignard solution was decomposed by the addition of 110 ml of 20% ammonium chloride solution. The reaction mixture was diluted with 180 ml ether. The phases were subsequently separated. The aqueous phase was extracted twice with 180 ml ether, dried over sodium sulphate, and the solvent was removed by distillation. The residue (25 g) was introduced on to a 6×30 cm column packed with silica gel, and was eluted first with 1:1 ether/n-hexane and then with 3:1 ether/n-hexane. 10.9 g of pure base was obtained, which was taken up in ether/2-butanone and treated with trimethylchlorosilane/water. 10.6 g of crystalline hydrochloride (1) were obtained.

Yield: 53% theoretical

Melting point: 156° C.–158° C.

Example 2

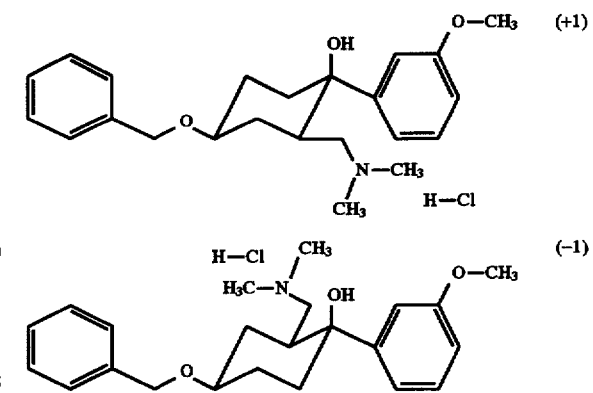

The enantiomers of (1):

(1S,2S,4R)-4-benzyloxy-2-dimethylaminomethyl-1-(3-methoxy-phenyl)-cyclohexanol hydrochloride
[(−)1]

and (1R,2R,4S)-4-benzyloxy-2-dimethylaminomethyl-1-(3-methoxy-phenyl)-cyclohexanol hydrochloride
[(+)1]

The base was released from compound (1) with dichloromethane/aqueous sodium hydroxide solution, the solution was dried, and the dichloromethane was distilled off under vacuum. The racemate was then separated on a chiral HPLC column. The bases of [(−)1] and [(+)1] were obtained; these were taken up in 2-butanone and treated with trimethylchlorosilane/water. The hydrochlorides were obtained.

[(−)1]
yield: 42.8% theoretical
melting point: 212° C.–214° C.
$[\alpha]^{RT}_D = -20.5°$ (water, c=1)

[(+)1]
yield: 40% theoretical
melting point: 213° C.–215° C.
$[\alpha]^{RT}_D = 21.8°$ (water, c=1)

Example 3

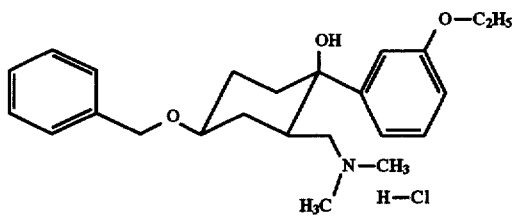

(1RS,2RS,4SR)-4-benzyloxy-2-dimethylaminomethyl-1-(methoxy-phenyl)-cyclohexanol hydrochloride (2)

1-bromo-3-ethoxy-benzene was reacted with 4-benzyloxy-2-dimethylaminomethyl-cyclohexanone corresponding to the conditions described in Example 1. The base obtained was purified with 6:1 ether/methanol via a silica gel column, subsequently taken up in 2-butanone and treated with trimethylchlorosilane/water. Compound (2) was obtained in a yield of 43% theoretical.

Melting point: 205° C.–207° C.

Example 4

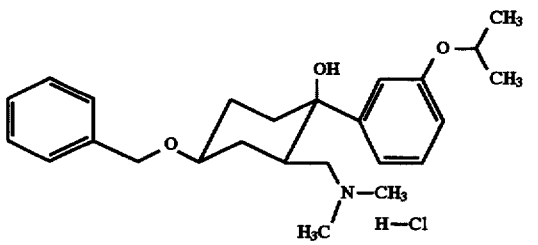

(1RS,2RS,4SR)-4-benzyloxy-2-dimethylaminomethyl-1-(3-isopropoxy-phenyl)-cyclohexanol hydrochloride (3)

1-bromo-3-isopropoxy-benzene was reacted with 4-benzyloxy-2-dimethylaminomethyl-cyclohexanone corresponding to the conditions described in Example 1. The base obtained was purified with 6:1 ether/methanol via a silica gel column, taken up in 2-butanone and treated with trimethylchlorosilane/water. Compound (3) was obtained in a yield of 35% theoretical.

Melting point: 166° C.–167° C.

Example 5

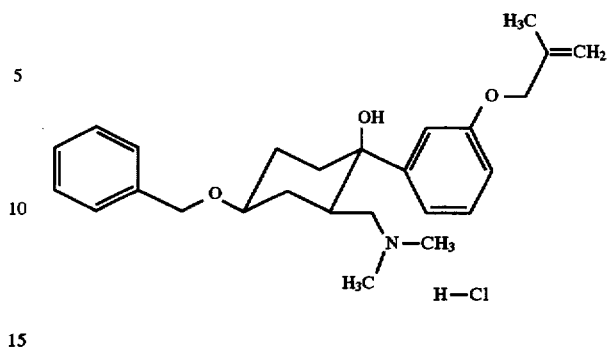

(1RS,2RS,4SR)-4-benzyloxy-2-dimethylaminomethyl-1-[3-(2-methyl-allyloxy)-phenyl]-cyclohexanol hydrochloride (4)

1-bromo-3-(2-methyl-allyloxy)-benzene, prepared by the alkylation of 1-bromo-3-hydroxy-benzene with 3-chloro-2-methyl-1-propene, was reacted with 4-benzyloxy-2-dimethylaminomethyl-cyclohexanone corresponding to the conditions described in Example 1. The base obtained was purified with 9:1 ether/methanol via a silica gel column, taken up in ether and treated with trimethylchlorosilane/water. Compound (4) was obtained.

Yield: 33% theoretical.

Melting point: 166° C.–167° C.

Example 6

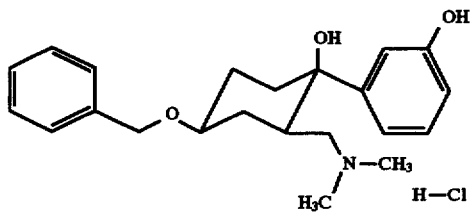

(1RS,2RS,4SR)-3-(4-benzyloxy-2-dimethylaminomethyl-1-hydroxy-cyclohexyl)-phenol hydrochloride (5)

(3-bromo-phenoxy)-tert-butyl-dimethyl-silane was reacted with 4-benzyloxy-2-dimethylaminomethyl-cyclohexanone corresponding to the conditions described in Example 1. The base obtained was purified with ethyl acetate via a silica gel column. The protective silyl group was subsequently split off with dilute hydrochloric acid in tetrahydrofuran, and the product was purified with 2:1 ethyl acetate/methanol via a silica gel column. It was then taken up in tetrahydrofuran and treated with concentrated hydrochloric acid. Compound (5) was obtained in an overall yield of 47% theoretical.

Melting point: 245° C.–247° C. (decompn.)

Example 7

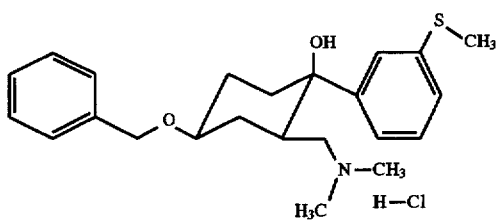

(1RS,2RS,4SR)-4-benzyloxy-2-
dimethylaminomethyl-1-(3-methyl-sulphanyl-
phenyl)-cyclohexanol hydrochloride (6)

1-bromo-3-methylsulphanyl-benzene was reacted with 4-benzyloxy-2-dimethylaminomethyl-cyclohexanone corresponding to the conditions described in Example 1. In departure from the conditions in Example 1, ether was used as the solvent and 1,2-dibromoethane was added to the batch in order to increase the yield. The base obtained was purified with n-hexane, diisopropyl ether and ether via a silica gel column, taken up in 2-butanone/ether, and treated with trimethylchlorosilane/water. The crystalline compound (6) was obtained in a yield of 43% theoretical.

Melting point: 194° C.-198° C. (decompn.)

Example 8

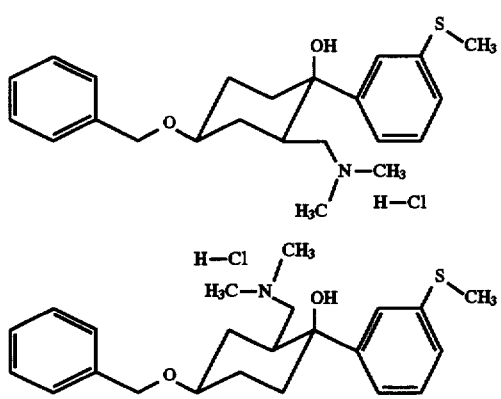

The enantiomers of (6):

(1S,2S,4R)-4-benzyloxy-2-[(dimethylamino)methyl]
-1-(3-methyl-sulphanyl-phenyl)-cyclohexanol
hydrochloride [(–)6]

and (1R,2R,4S)-4-benzyloxy-2-[(dimethylamino)methyl]
-1-(3-methyl-sulphanyl-phenyl)-cyclohexanol
hydrochloride [(+)6]

The base was released from compound (6) with methylene chloride/aqueous sodium hydrogen carbonate solution, the solution was dried, and the methylene chloride was distilled off under vacuum. The racemate was then separated on a chiral HPLC column. The bases of compounds [(–)6] and [(+)6] were obtained; these were taken up in 2-butanone and small amounts of diisopropyl ether and were treated with trimethylchlorosilane/water. The hydrochlorides were obtained.

[(–)6]
yield: 57% theoretical melting point: 195° C.-196° C.
$[\alpha]^{RT}_D = -19°$ (water, c=1)

[(+)6]
yield: 50% theoretical
melting point: 194° C.-194.5° C.
$[\alpha]^{RT}_D = 20°$ (water, c=1)

Example 9

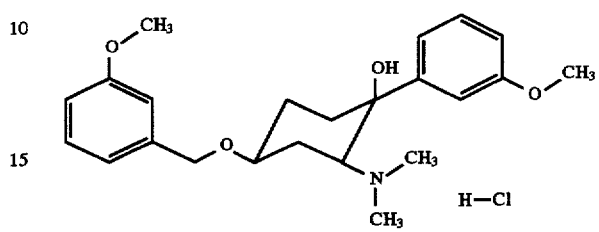

(1RS,2RS,4SR)-2-dimethylaminomethyl-4-(3-
methoxybenzyloxy)-1-(3-methoxyphenyl)-
cyclohexanol hydrochloride (7)

1st step 4-(3-methoxybenzyloxy)-cyclohexanone (8)

4.4 g of 60% sodium hydride in mineral oil (0.11 mole) were stirred in 35 ml absolute dimethylformamide under a nitrogen atmosphere. 15.7 g (0.1 mole) 1,4-dioxaspiro[4.5]decan-8-ol were dissolved in 65 ml dimethylformamide. This solution was added drop-wise to the sodium hydride suspension. 16 ml 1-chloromethyl-3-methoxybenzene (0.11 mole), dissolved in 25 ml dimethylformamide, were then added. The mixture was stirred for 30 minutes at 60° C., poured on to ice, extracted with ether and dried over sodium sulphate. After evaporation of the solvent, 29 g of crude product were obtained. This was stirred for 1 hour with a mixture of 190 ml tetrahydrofuran and 50 ml of concentrated hydrochloric acid in order to cleave the acetal. The product was diluted with saturated sodium chloride solution, and the phases were separated, extracted with ether and dried. After removal of the solvent by distillation, compound (8) which was obtained was purified with diisopropyl ether via a silica gel column.

Yield 14 g (60% theoretical)

2nd step

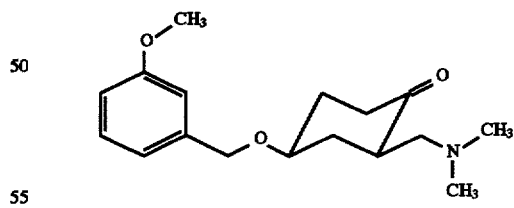

2-dimethylaminomethyl-4-(3-methoxybenzyloxy)-
cyclohexanone (9)

11.8 g (50 mmole) of compound (8), 0.84 g (28 mmole) paraformaldehyde and 2.26 g (28 mmole) dimethylamine hydrochloride were dissolved in 20 ml acetic acid and stirred for 15 minutes in a bath at 105° C. After evaporating off the solvent, the mixture was adjusted to an alkaline pH with aqueous sodium hydroxide solution and the Mannich base was extracted with dichloromethane. The solution was dried and the solvent was distilled off. 12.1 g (80% theoretical) of compound (9) were obtained.

3rd step (1RS,2RS,4SR)-2-dimethylaminomethyl-4-(3-methoxybenzyloxy)-1-(3-methoxyphenyl)-cyclohexanol hydrochloride (7)

The Mannich compound (9) was reacted with 1-bromo-3-methoxy-benzene corresponding to the conditions described in Example 1. The mixture of bases which was obtained (substituent in the 4-position cis and trans to OH) was introduced on to a silica gel column and eluted in succession with diisopropyl ether, ether and ethyl acetate/methanol. The two isomers were subsequently purified with 7:1 ether/methanol via a silica gel column, taken up in 2-butanone, and treated with trimethylchlorosilane/water, with the addition of ether if necessary. The cis form of compound (7) was obtained in a yield of 7.5%, melting point 151° C.–153° C.; the trans form of compound (7) was obtained in a yield of 20% theoretical, melting point 133° C.–135° C.

Example 10

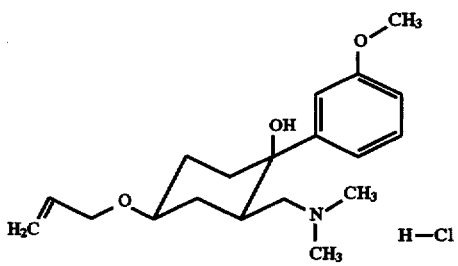

(1RS,2RS,4SR)-4-allyloxy-2-dimethylaminomethyl-1-(3-methoxyphenyl)-cyclohexanol hydrochloride (10)

1st step 8-allyloxy-1,4-dioxa-spiro[4.5]decane (11)

23.7 g (150 mmole) 1,4-dioxa-spiro[4.5]decan-8-ol were dissolved in 120 ml absolute dimethylformamide under a nitrogen atmosphere. After adding 7.9 g of 50% sodium hydride in mineral oil (165 mmole), the mixture was stirred for 1 hour at 20° C. After adding 14.3 ml allyl bromide (165 mmole), the mixture was heated to 70° C. and stirred for 1 hour. Thereafter it was treated with 160 ml water and was extracted at 10° C.–15° C., three times with ether, once with water and once with saturated sodium chloride solution. After removing the solvent by distillation, 24 g of crude product (81% theoretical) were obtained.

2nd step 4-allyloxy-cyclohexanone (12)

19.8 g of compound (11) (0.1 mmole) were stirred for 2 hours at room temperature with 120 ml ether and 40 ml of 6N hydrochloric acid. The mixture was then neutralised with sodium hydrogen carbonate, extracted three times with ether, and the ether solution was dried over sodium sulphate. After removing the solvent by distillation, 15.2 g of crude product were obtained; the product was purified with 3:1 diisopropyl ether/n-hexane via a silica gel column.

Yield: 12.8 g (83% theoretical)

3rd step

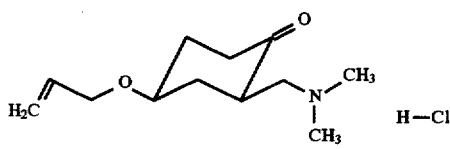

4-allyloxy-2-dimethylaminomethyl-cyclohexanone hydrochloride (13)

15.5 g of compound (12) (100 mmole), 1.5 g (50 mmole) paraformaldehyde and 4.1 g (50 mmole) dimethylamine hydrochloride were stirred for 25 minutes in 30 ml acetic acid in a bath at 105° C. The acetic acid was distilled off under vacuum, and the residue was dissolved in 110 ml 2-butanone. Compound (13) was obtained in a yield of 77% theoretical, melting point 125° C.–127° C.

4th step (1RS,2RS,4SR)-4-allyloxy-2-dimethylaminomethyl-1-(3-methoxyphenyl)-cyclohexanol hydrochloride (10)

Base (13) was reacted with 1-bromo-3-methoxy-benzene corresponding to the conditions described in Example 1. The base obtained was purified with 1:4 ether/diisopropyl ether via a silica gel column and was taken up in 1:1 2-butanone/ether. After adding trimethylchlorosilane/water, compound (10) was obtained in a yield of 37% theoretical.

melting point: 88° C.–94° C.

Example 11

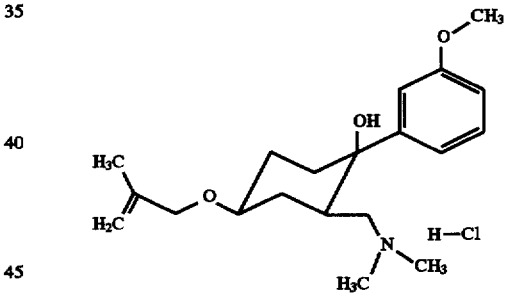

(1RS,2RS,4SR)-2-dimethylaminomethyl-1-(3-methoxy-phenyl)-4-(2-methyl-2-allyloxy)-cyclohexanol hydrochloride (14)

1st step 8-(2-methyl-allyloxy)-1,4-dioxa-spiro[4.5]decane (15)

The reaction to form compound (15) was carried out with 1,4-dioxa-spiro[4.5]decan-8-ol and 2-methyl-allyl bromide corresponding to the conditions described for Example 10 step 1. Compound (15) which was obtained was purified with 1:2 diisopropyl ether/n-hexane via a silica gel column. Compound (15) was obtained as a light-coloured oil in a yield of 81% theoretical.

2nd step 4-(2-methyl-allyloxy)-cyclohexanone (16)

The acetal cleavage of compound (15) was effected corresponding to the conditions described for Example 10, step 2. Compound (16) which was obtained was purified with 2:1 diisopropyl ether/n-hexane via a silica gel column. Compound (16) was obtained as an oil in a yield of 62% theoretical.

3rd step

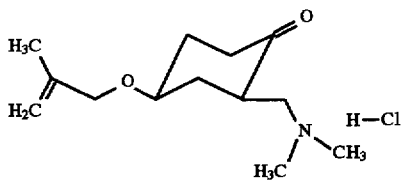

2-dimethylaminomethyl-4-(2-methyl-2-allyloxy) cyclohexanone hydrochloride (17)

The Mannich reaction was carried out with compound (16) and dimethylamine hydrochloride, corresponding to the conditions described in Example 10, step 3. Compound (17) was obtained from 2-butanone in a yield of 38% theoretical.

melting point: 111° C.–112° C.

4th step (1RS,2RS,4SR)-2-dimethylaminomethyl-1-(3-methoxy-phenyl)-4-(2-methyl-2-allyloxy)-cyclohexanol hydrochloride (14)

Compound (17) was reacted with 1-bromo-3-methoxybenzene corresponding to the conditions described in Example 1. The base obtained was purified with 1:1 ethyl acetate/methanol via a silica gel column and was taken up in ether. After adding trimethylchlorosilane/water, compound (14) was obtained in a yield of 36% theoretical.

melting point: 112° C.–114° C.

Example 12

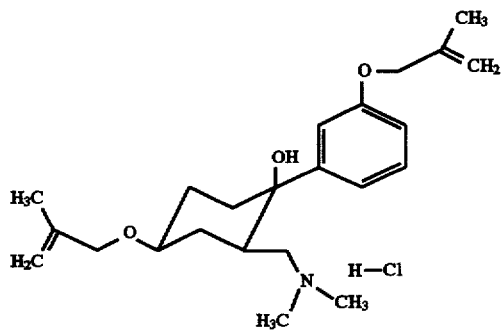

(1RS,2RS,4SR)-2-dimethylaminomethyl-4-(2-methyl-2-allyloxy)-1-[3-(2-methyl-2-allyloxy)-phenyl]-cyclohexanol hydrochloride (18)

Base (17) and 1-bromo-3-(2-methyl-allyloxy)-benzene were reacted corresponding to the conditions described in Example 1. The crude product was introduced on to a silica gel column and eluted with diisopropyl ether/ether. The mixture obtained, which was epimeric with respect to position 1, was separated into the cis and trans diastereoisomers by HPLC and then taken up in 2-butanone/diisopropyl ether. After adding trimethylchlorosilane/water, compound (18) was obtained in a yield of 18% theoretical.

melting point: 151° C.–152.5° C.

Example 13

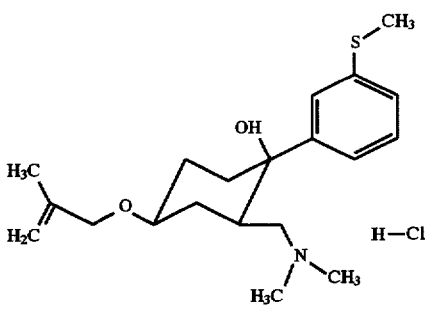

(1RS,2RS,4SR)-2-dimethylaminomethyl-4-(2-methyl-2-allyloxy)-1-(3-methylsulphanyl-phenyl)-cyclohexanol hydrochloride (19)

The base of compound (17) and 1-bromo-3-methylsulphanyl-benzene were reacted corresponding to the conditions described in Example 1. In departure from the conditions in Example 1, ether was used as the solvent and 1,2-dibromoethane was added to the batch in order to increase the yield. The crude product obtained was purified with 1:1 diisopropyl ether/ether via a silica gel column, and was taken up in ethyl acetate. After adding trimethylchlorosilane/water, compound (19) was obtained in a yield of 40% theoretical.

Melting point: 146° C.–150° C.

Example 14

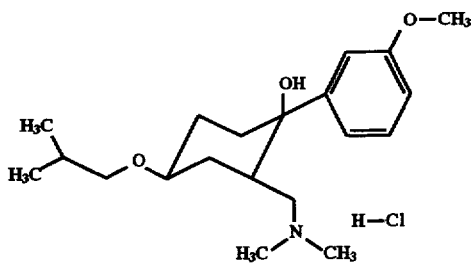

(1RS,2RS,4SR)-2-dimethylaminomethyl-4-isobutoxy-1-(3-methoxy-phenyl)-cyclohexanol hydrochloride (20)

1st step 4-isobutoxy-cyclohexanone (21)

16.9 g (0.1 mole) of compound (16) were dissolved in 90 ml methanol. After adding 1.8 g of palladinised charcoal (10% Pd content), the solution was hydrogenated at room temperature and normal pressure. The catalyst was then removed and the solvent was distilled off under vacuum. The 15 g of crude product which were obtained were stirred for 1 hour at room temperature with 60 ml ether and 30 ml of 4N hydrochloric acid. This was followed by neutralisation with sodium hydrogen carbonate, separation of the ether phase, and extracting twice with ether. The ethereal solution was dried over sodium sulphate and the ether was distilled off. The 10.5 g of oil obtained were purified with 1:1 diisopropyl ether/n-hexane via a silica gel column. 6.85 g of compound (21) were obtained in a yield of 40% theoretical.

2nd step

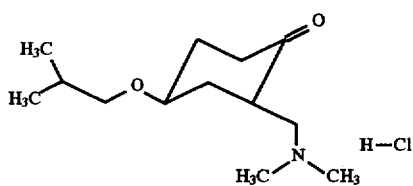

2-dimethylaminomethyl-4-isobutoxy-cyclohexanone hydrochloride (22)

Compound (21) was reacted with dimethylamine hydrochloride corresponding to the conditions described in Example 10, step 3. The compound of formula (22) was obtained from 2-butanone in a yield of 53% theoretical.

melting point: 113° C.–115° C.

3rd step (1RS,2RS,4SR)-2-dimethylaminomethyl-4-isobutoxy-1-(3-methoxy-phenyl)-cyclohexanol hydrochloride (20)

The base of compound (22) was reacted with 1-bromo-3-methoxy-benzene corresponding to the conditions described in Example 1. The base obtained was purified with 1:1 ethyl acetate/methanol via a silica gel column, and was taken up in ether. After adding trimethylchlorosilane/water, compound (20) was obtained in a yield of 38% theoretical.

Melting point: 112° C.–116° C.

Example 15

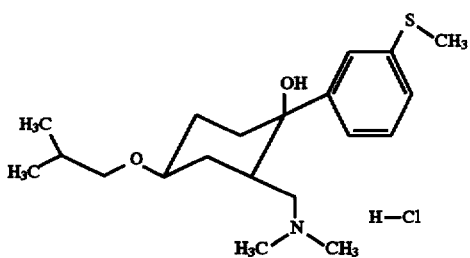

(1RS,2RS,4SR)-2-dimethylaminomethyl-4-isobutoxy-(3-methylsulphanyl-phenyl)-cyclohexanol hydrochloride (23)

Compound (22) was reacted with 1-bromo-3-methylsulphanyl-benzene corresponding to the conditions described in Example 1. In departure from the conditions described in Example 1, ether was used as the solvent and 1,2-dibromoethane was added to the batch in order to increase the yield. The crude product obtained was purified with diisopropyl ether via a silica gel column, and was taken up in tetrahydrofuran/ether. The crystals obtained after adding trimethylchlorosilane/water were recrystallised from ethyl acetate. Compound (23) was obtained in a yield of 32% theoretical.

Melting point: 120° C.–122° C.

Example 16

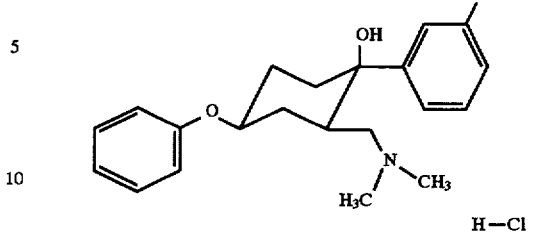

(1RS,2RS,4SR)-2-dimethylaminomethyl-1-(3-methoxy-phenyl)-4-phenoxy-cyclohexanol hydrochloride (24)

1st step 8-phenoxy-1,4-dioxa-spiro[4.5]decane (25)

440 mg of 60% sodium hydride in mineral oil (0.12 mmole) were stirred in 9 ml absolute dimethylformamide under a nitrogen atmosphere. 1.1 g (0.12 mmole) phenol were added, followed by 3.1 g (10 mmole) toluene-4-sulphonic acid-1,4-dioxaspiro[4.5]dec-8-yl ester (Gray et al., J. Org. Chem., 35, (1970), 1525–1533), dissolved in 6 ml dimethylformamide. The batch was stirred for 2 hours at a temperature between 80° C. and 85° C. After cooling, the batch was poured on to ice and extracted with ether, and the solution was washed with dilute aqueous sodium hydroxide solution and dried over sodium sulphate. After evaporating off the solvent, the crude product was purified with diisopropyl ether via a silica gel column. 1.27 g (54% theoretical) of compound (25) were obtained as an oil.

2nd step 4-phenoxy-cyclohexanone (26)

11.7 g (50 mmole) 8-phenoxy-1,4-dioxa-spiro[4.5]decane (25) were dissolved in 250 in ether. 50 ml water and 37.5 ml concentrated hydrochloric acid were added with stirring. The mixture was stirred for 2 hours and allowed to stand overnight. After subsequent phase separation the mixture was extracted with ether and washed with saturated common salt solution, and the solvent was distilled off. 9 g (91% theoretical) of compound (26) were obtained.

3rd step

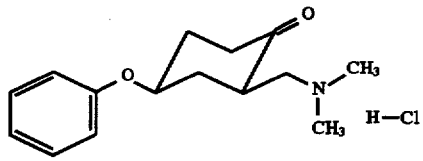

2-dimethylaminomethyl-4-phenoxy-cyclohexanone hydrochloride (27)

9.5 g (50 mmole) 4-phenoxy-cyclohexanone (26), 0.765 g (25 mmole) paraformaldehyde and 2.08 g (25 mmole) dimethylamine hydrochloride were heated for 20 minutes in 17 ml acetic acid in an oil bath at a temperature of 105° C. Thereafter the solvent was distilled off under vacuum, the residue was treated twice with 2-butanone, and the 2-butanone was subsequently distilled off under vacuum. The salt obtained was taken up in 30 ml 2-butanone. 2.85 g of compound (27) (40% theoretical) were obtained.

melting point 104° C.–106° C. (40% theoretical)
4th step (1RS,2RS,4SR)-2-dimethylaminomethyl-1-(3-
methoxy-phenyl)-4-phenoxy-cyclohexanol
hydrochloride (24)

The base of compound (27) was reacted with 1-bromo-3-methoxy-benzene corresponding to the conditions described in Example 1. The base obtained was purified with 6:1 ethyl acetate/methanol via a silica gel column and was taken up in 2-butanone. After adding trimethylchlorosilane/water, compound (24) was obtained in a yield of 47% theoretical.

melting point: 216° C.–218° C.

Example 17

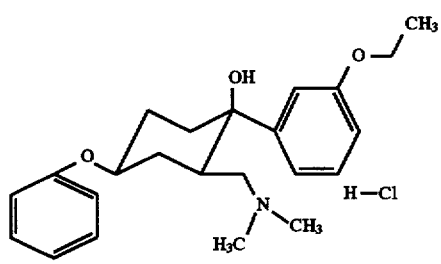

(1RS,2RS,4SR)-2-dimethylaminomethyl-1-(3-
ethoxy-phenyl)-4-phenoxy-cyclohexanol
hydrochloride (28)

The base of compound (27) was reacted with 1-bromo-3-methoxy-benzene corresponding to the conditions described in Example 1. The base obtained was purified with 6:1 ethyl acetate/methanol via a silica gel column and was taken up in 2-butanone. After adding trimethylchlorosilane/water, compound (28) was obtained in a yield of 49% theoretical.

melting point: 237° C.–239° C.

Example 18

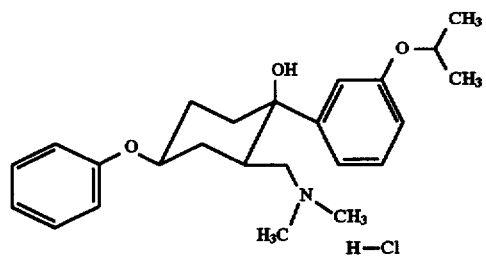

(1RS,2RS,4SR)-2-dimethylaminomethyl-1-(3-
isopropoxy-phenyl)-4-phenoxy-cyclohexanol
hydrochloride (29)

The base of compound (27) was reacted with 1-bromo-3-propoxy-benzene corresponding to the conditions described in Example 1. The base obtained was purified with 6:1 ethyl acetate/methanol via a silica gel column and was taken up in 2-butanone. After adding trimethylchlorosilane/water, compound (29) was obtained in a yield of 38% theoretical.

melting point: 200° C.–202° C.

Example 19

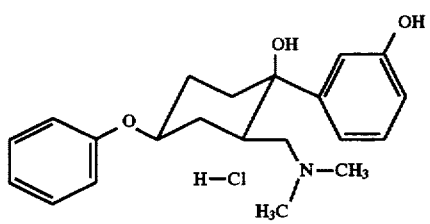

(1RS,2RS,4SR)-3-(2-dimethylaminomethyl)-1-
hydroxy-4-phenoxy-cyclohexyl)-phenol
hydrochloride (30)

The base of compound (27) was reacted with 1-bromo-3-benzyl-oxy-benzene corresponding to the conditions described in Example 1. The phenol, which was protected with a benzyl group, was obtained in a yield of about 50% theoretical (crude product). It was subsequently taken up in methanol, palladinised charcoal (10% Pd content) was added, and the benzyl group was split off by hydrogenation at room temperature under normal pressure. The base obtained was purified with 6:1 ethyl acetate/methanol via a silica gel column and was taken up in 2-butanone. After adding trimethylchlorosilane/water, compound (30) was obtained in a yield of 50% theoretical.

melting point: 220° C.–222° C.

Example 20

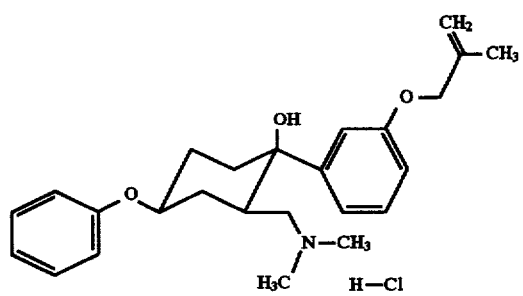

(1RS,2RS,4SR)-2-dimethylaminomethyl-1-[3-(2-
methyl-allyloxy)-phenyl]-4-phenoxy-cyclohexanol
hydrochloride (31)

The base of compound (27) was reacted with 1-bromo-3-(2-methyl-allyloxy)-benzene corresponding to the conditions described in Example 1. The base obtained was purified with ether via a silica gel column and was taken up in 2-butanone. After adding trimethylchlorosilane/water, compound (31) was obtained in a yield of 51% theoretical.

melting point: 193° C.–195° C.

Example 21

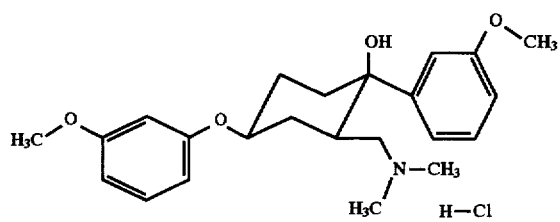

(1RS,2RS,4SR)-2-dimethylaminomethyl-4-(3-methoxyphenoxy)-1-(3-methoxy-phenyl)-cyclohexanol hydrochloride (32)

1st step 4-(3-methoxy-phenoxy)-cyclohexanone (33)

3-methoxy-phenol was reacted with toluene-4-sulphonic acid-1,4-dioxa-spiro[4.5]dec-8-yl ester corresponding to the conditions described in Example 16, step 1. The crude product was subjected, without purification, to an acetal cleavage corresponding to the conditions described in Example 16, step 2. The ketone obtained was purified with diisopropyl ether on a silica gel column. Compound (33) was obtained in a yield of 57% theoretical.

2nd step

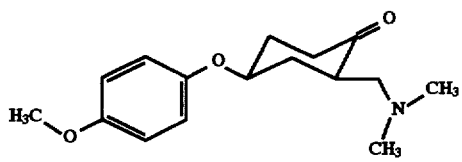

2-dimethylaminomethyl-4-(3-methoxy-phenoxy)-cyclohexanone (34)

Compound (33) was reacted with diethylamine hydrochloride corresponding to the conditions described in Example 16, step 3. For the work-up, the acetic acid was distilled off, and the residue was dissolved in water and extracted with ether. The pH of the aqueous phase was made alkaline with aqueous sodium hydroxide solution and the product was extracted with dichloromethane. The solvent was removed by distillation and compound (34) was obtained as a cis-trans mixture in a yield of 50% theoretical.

3rd step (1RS,2RS,4SR)-2-dimethylaminomethyl-4-(3-methoxyphenoxy)-1-(3-methoxy-phenyl)-cyclohexanol hydrochloride (32)

Compound (34) was reacted with 1-bromo-3-methoxy-benzene corresponding the conditions described in Example 1. The mixture of bases, which was epimeric with respect to position 1, was successively eluted with diisopropyl ether and ethyl acetate on a silica gel column. The fraction which was enriched in the cis form was then purified with 7:1 ether/methanol via a silica gel column. It was then taken up in 2-butanone and trimethylchlorosilane/water was added. Compound (32) (position 4 cis to OH) was obtained in a yield of 10% theoretical.

melting point: 208° C.–210° C.

Example 22

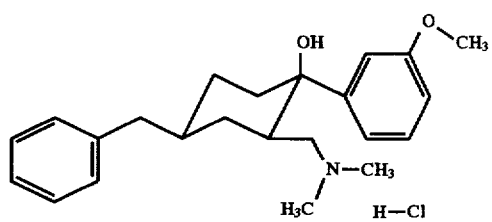

(1RS,2RS,4SR)-4-benzyl-2-dimethylaminomethyl-1-(3-methoxy-phenyl)-cyclohexanol hydrochloride (35)

1st step

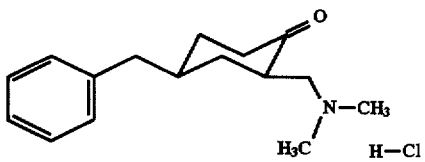

4-benzyl-2-dimethylaminomethyl-cyclohexanone hydrochloride (36)

4-benzylcyclohexanone was reacted with dimethylamine hydrochloride corresponding to the conditions described in Example 10, step 3. Compound (36) was obtained in crystalline form in a yield of 50% theoretical.

melting point: 136° C.–138° C.

2nd step (1RS,2RS,4SR)-4-benzyl-2-dimethylaminomethyl-1-(3-methoxy-phenyl)-cyclohexanol hydrochloride (35)

The base of compound (36) was reacted with 1-bromo-3-methoxy-benzene corresponding to the conditions described in Example 1. The base obtained was purified with 7:1 ether/methanol via a silica gel column and was taken up in ether. After adding trimethylchlorosilane/water, compound (35) was obtained in a yield of 55% theoretical.

melting point: 138° C.–142° C.

Example 23

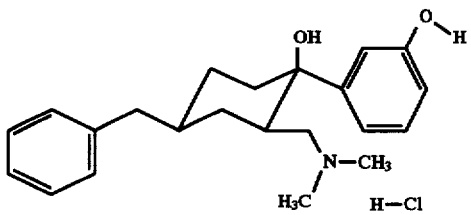

(1RS,2RS,4SR)-3-(4-benzyl-2-dimethylaminomethyl-1-hydroxy-cyclohexyl)-phenol hydrochloride (37)

1st step

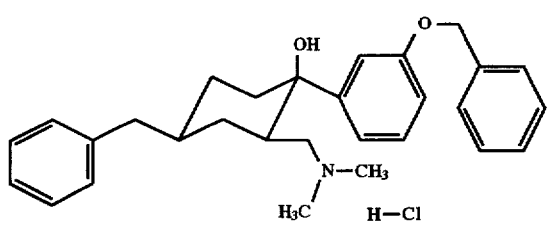

4-benzyl-1-(3-benzyloxyphenyl)-2-dimethylaminomethyl-cyclohexanol (38)

The base of compound (36) was reacted with 1-bromo-3-benzyloxy-benzene corresponding to the conditions described in Example 1. The base obtained was purified with 7:1 ether/methanol via a silica gel column.

Yield of compound (38): 76% theoretical

2nd stage

(1RS,2RS,4SR)-3-(4-benzyl-2-dimethylaminomethyl-1-hydroxy-cyclohexyl)-phenol hydrochloride (37)

Compound (38) was dissolved in methanol. After adding palladinised charcoal (10% Pd), the solution was hydrogenated at room temperature and normal pressure. After filtering off the catalyst and removing the solvent by distillation the product was taken up in ether. The hydrochloride was obtained by the subsequent addition of trimethylchlorosilane/water. After recrystallisation from 2-butanone/water, compound (37) was obtained in a yield of 61% theoretical.

melting point: 187° C.–192° C.

Example 24

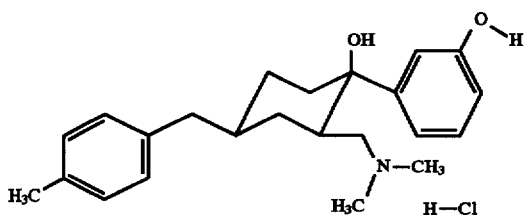

(1RS,2RS,4SR)-3-[2-dimethylaminomethyl-1-hydroxy-4-(4-methyl-benzyl)-cyclohexyl]-phenol hydrochloride (39)

1st step

4-hydroxy-4-(4-methyl-benzyl)-cyclohexanone (40)

Small amounts of a solution of 22.2 g 1-bromoethyl-4-methyl-benzene (120 mmole) in 80 ml ether were added drop-wise to 2.9 g (120 mmole) magnesium turnings. After the Grignard reaction had commenced, the rest of the solution was added and the mixture was boiled for 30 minutes under reflux. It was then cooled to 0° C.–10° C. and a solution of 15.7 g (100 mmole) 1,4-dioxa-spiro[4.5]decan-8-one, dissolved in 35 ml tetrahydrofuran and 70 ml ether, was added at this temperature. The mixture was boiled for 2 hours under reflux. After cooling to 0° C.–10° C., 80 ml of a 20% ammonium chloride solution were added and the phases were separated. This was followed by extraction with ether, drying over sodium sulphate and removal of the solvent by distillation. 27.5 g of crude product were obtained, which were dissolved in 300 ml ether, treated with 200 ml of 50:50 concentrated hydrochloric acid/water, and stirred for 3 hours at room temperature. This was followed by dilution with saturated common salt solution. After phase separation, the product was extracted with ether and dried over sodium sulphate. The solvent was then removed by distillation and the product was purified with 2:1 ether/hexane via a silica gel column.

The yield of compound (40) was 11.5 g (53% theoretical)

2nd step

4-(4-methyl-benzyl)-cyclohexanone (41)

10.9 g (50 mmole) of compound (40) were dissolved in 250 ml formic acid and boiled for 3 hours under reflux. A mixture of olefines was obtained. The formic acid was distilled off under vacuum and the olefines were purified with 1:1 ether/hexane via a silica gel column. 7.5 g of the mixture of olefines was obtained. This was dissolved in ethanol, and after adding palladinised charcoal (10% Pd content) was hydrogenated at room temperature and normal pressure. After filtering off the catalyst and removing the solvent by distillation, 7.8 g of ketone were obtained. Cleavage of the acetal and subsequent work-up were effected corresponding to the conditions described in step 1. 6.7 g ketone were obtained, which were purified with 1:2 ether/hexane via a silica gel column.

The yield of compound (41) was 5.15 g; 51% theoretical.

3rd step

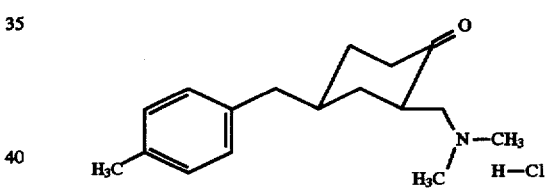

2-dimethylaminomethyl-4-(4-methyl-benzyl)-cyclohexanone hydrochloride (42)

Compound (41) was reacted with dimethylamine hydrochloride corresponding to the conditions described in Example 10, step 3. Compound (42) was obtained in crystalline form in a yield of 46% theoretical.

melting point: 124° C.–127° C.

4th step

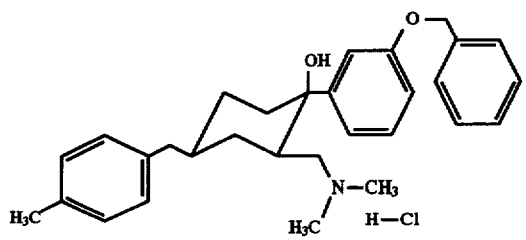

1-(3-benzyloxyphenyl)-2-dimethylaminomethyl-4-(4-methyl-benzyl)-cyclohexanol (43)

1-bromo-3-benzyloxy-benzene and the base of compound (42) were reacted corresponding to the conditions described in Example 1. The product obtained was dissolved in ether/hexane and the base was extracted with 10% acetic acid. After adjusting to an alkaline pH, compound (43) was extracted with ether and dried over sodium sulphate. After removing the solvent by distillation the product was purified with 1:1 ether/diisopropyl ether via an alumina column (3.6% water). Compound (43) was obtained in a yield of 65% theoretical.

5th step (1RS,2RS,4SR)-3-[2-dimethylaminomethyl-1-hydroxy-4-(4-methyl-benzyl)-cyclohexyl]-phenol hydrochloride (39)

Compound (43) was hydrogenated corresponding to the conditions described in Example 23, step 2. The product was then taken up in 1:1 dichloromethane/ether and tetramethylchlorosilane/water was added. After recrystallisation from 2-butanone/water, compound (39) was obtained in a yield of 56% theoretical.

melting point: 188° C.–191° C.

Example 25

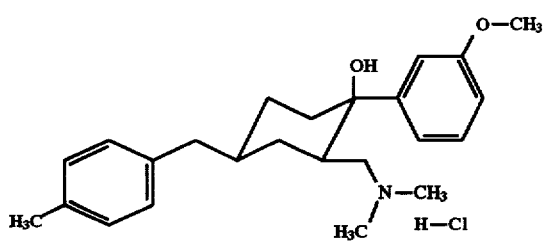

(1RS,2RS,4SR)-2-dimethylaminomethyl-1-(3-methoxy-phenyl)-4-(4-methylbenzyl)-cyclohexanol hydrochloride (44)

The base of compound (42) was reacted with 1-bromo-3-methoxy-benzene corresponding to the conditions described in Example 1. The base obtained was purified with 7:1 ether/methanol via a silica gel column and was taken up in ether. After adding trimethylchlorosilane/water, compound (44) was obtained in a yield of 39% theoretical.

melting point: 116° C.–122° C.

Example 26

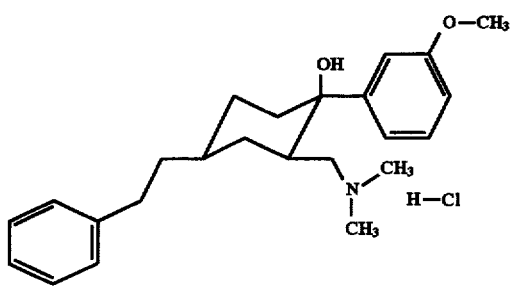

(1RS,2RS,4SR)-2-dimethylaminomethyl-1-(3-methoxy-phenyl)-4-phenylethyl-cyclohexanol hydrochloride (45)

1st step 4-hydroxy-4-phenylethyl-cyclohexanone (46)

(2-chloroethyl)-benzene was reacted with 1,4-dioxa-spiro[4.5]decan-8-one corresponding to the conditions described in Example 24, step 1. The product was purified with 5:1 ether/n-hexane on a silica gel column. Compound (46) was obtained in a yield of 71% theoretical.

2nd step 4-(phenethyl)-cyclohexanone (47)

Compound (46) was dehydrated and hydrogenated corresponding to the conditions described in Example 24, step 2. After dehydration, the mixture of olefines obtained was purified with 3:1 diisopropyl ether/n-hexane via a silica gel column. The compound of formula (47) which was obtained after hydrogenation was purified with 1:1 diisopropyl ether/n-hexane via a silica gel column. Compound (47) was obtained in a yield of 54% theoretical.

3rd step

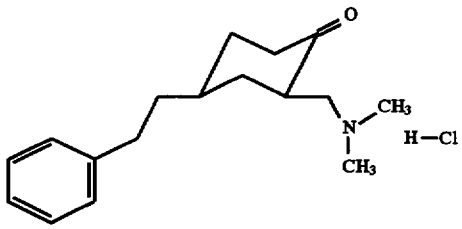

2-dimethylaminomethyl-4-(phenethyl)-cyclohexanone hydrochloride (48)

20.2 g (0.1 mole) of compound (47), 1.5 g (0.05 mole) paraformaldehyde and 4.07 g (0.05 mole) dimethylamine hydrochloride were dissolved in 40 ml acetic acid and heated in a bath at 105° C. for 20 minutes with stirring. The acetic acid was subsequently distilled off under vacuum, and the residue was dissolved in 100 ml water and extracted with ether. The aqueous phase was adjusted to a pH of 11 with aqueous sodium hydroxide solution and the Mannich base was extracted with dichloromethane. After drying and removal of the solvent by distillation, 17.5 g of the base of compound (47) were obtained, and were taken up in 2-butanone. 17.2 g of compound (48) were obtained in a yield of 58% theoretical by the subsequent addition of trimethylchlorosilane/water.

melting point: 159° C.–160° C.

4th step (1RS,2RS,4SR)-2-dimethylaminomethyl-1-(3-methoxy-phenyl)-4-phenylethyl-cyclohexanol hydrochloride (45)

The base of compound (48) was reacted with 1-bromo-3-methoxy-benzene corresponding to the conditions described in Example 1. The base obtained was purified firstly with 7:1 ether/methanol via a silica gel column and subsequently via HPLC. It was taken up in 2-butanone and trimethylchlorosilane/water was added, with the addition of ether if necessary. Compound (45) was obtained in a yield of 40% theoretical.

melting point: 170° C.–173° C.

Example 27

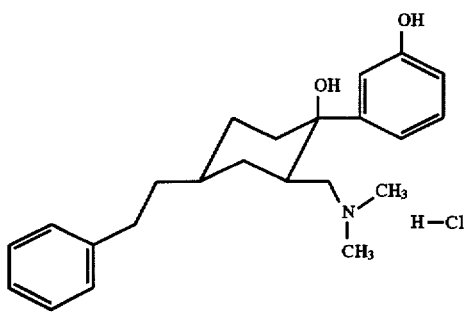

(1RS,2RS,4SR)-3-(2-dimethylaminomethyl-1-hydroxy-4-phenethyl-cyclohexyl)-phenol hydrochloride (49)

1st step

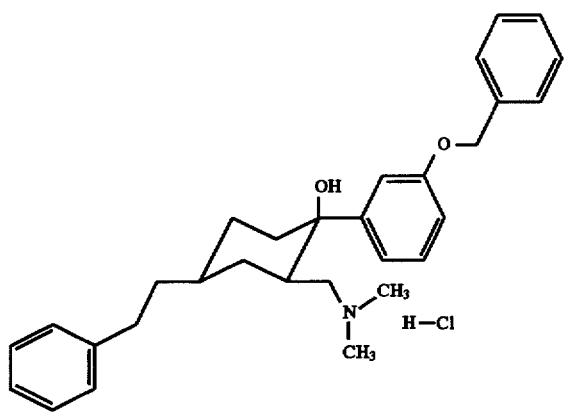

1-(3-benzyloxyphenyl)-2-dimethylaminomethyl-4-phenethyl-cyclohexanol (50)

The base of compound (48) was reacted with 1-bromo-3-benzyloxy-benzene corresponding to the conditions described in Example 1. The base obtained was purified with 6:1 ether/methanol via a silica gel column. Compound (50) was obtained in a yield of 87% theoretical.

2nd step (1RS,2RS,4SR)-3-(2-dimethylaminomethyl-1-hydroxy-4-phenethyl-cyclohexyl)-phenol hydrochloride (49)

Compound (50) was hydrogenated corresponding to the conditions described in Example 23, step 2. The base obtained was converted into the hydrochloride with trimethylchlorosilane/water. Compound (49) was obtained in a yield of 63% theoretical.

melting point: 254° C.–256° C.

Example 28

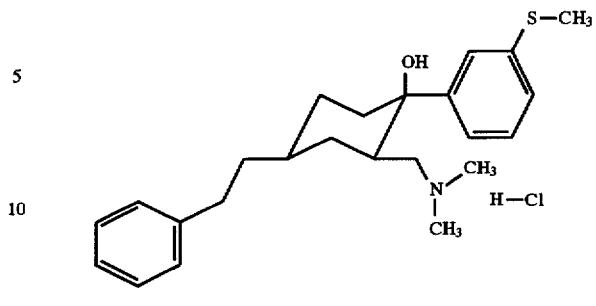

(1RS,2RS,4SR)-2-dimethylaminomethyl-1-(3-methylsulphanyl-phenyl)-4-phenethyl-1-cyclohexanol hydrochloride (51)

The base of compound (48) was reacted with 1-bromo-3-methyl-sulphanyl-benzene corresponding to the conditions described in Example 1. In departure from the conditions described in Example 1, ether was used as the solvent and 1,2-dibromoethane was added to the reaction batch in order to increase the yield. The crude product was purified with diisopropyl ether via a silica gel column and was taken up in 2-butanone. After the addition of trimethylchlorosilane/water, compound (51) was obtained in a yield of 23% theoretical.

melting point: 161° C.–163° C.

Example 29

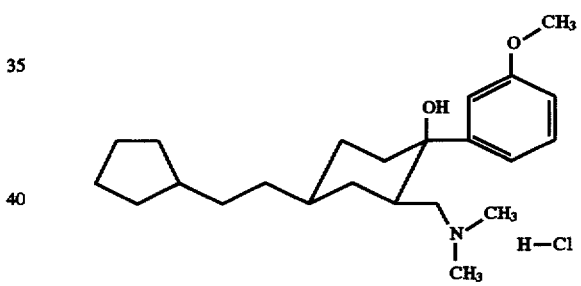

(1RS,2RS,4SR)-4-(cyclopentyl-ethyl)-2-dimethylaminomethyl-1-(3-methoxyphenyl)-cyclohexanol hydrochloride (52)

1st step (cyclopentylethyltriphenylphosphonium) bromide (53)

17.7 g (100 mmole) (2-bromoethyl)-cyclopentane, 32.5 g (124 mmole) triphenylphosphine and 100 ml toluene were boiled for 56 hours under reflux. The mixture was stirred overnight at room temperature. The crystals formed were filtered off by suction, washed with ether and dried under vacuum. The yield of compound (53) was 35.6 g (82% theoretical).

melting point: 210° C.–213° C.

2nd step 8-(2-cyclopentyl-ethylidene)-1,4-dioxa-spiro[4.5]decane (53)

The reaction was conducted in a nitrogen atmosphere with the exclusion of moisture. 21.9 g (50 mmole) of compound

(52) were added to 5.6 g (50 mmole) potassium tert-butylate in 400 ml toluene. The mixture was stirred for 30 minutes at room temperature and for 1 hour at 80° C., and was subsequently cooled to 60° C. 7.8 g (50 mmole) 1.4-dioxaspiro[4.5]decan-8-one were added. The mixture was then stirred for 18 hours at 60° C. and cooled. 100 ml water were added drop-wise. The organic phase was separated off, the aqueous phase was extracted twice with toluene and dried over sodium sulphate, and the solvent was removed by distillation. 29 g oil were obtained, which was purified with 1:4 diisopropyl ether/n-hexane on a silica gel column.

The yield was 6.8 g (58% theoretical) of compound (54).

3rd step (2-cyclopentyl-ethyl)-cyclohexanone (55)

9.45 g (40 mmole) of compound (54) were dissolved in 50 ml methanol, treated with 1.3 g palladinised charcoal (10% Pd content) and hydrogenated at normal pressure and room temperature. The catalyst was separated off and the residue was stirred with 10 parts tetrahydrofuran and 4 parts of 50:50 concentrated hydrochloric acid/water. The product was then neutralised with sodium hydrogen carbonate, extracted with ether and dried over sodium sulphate, and the solvent was distilled off. The oil obtained was purified with 1:9 ether/n-hexane via a silica gel column. Compound (55) was obtained in a yield of 5.9 g (76% theoretical).

4th step

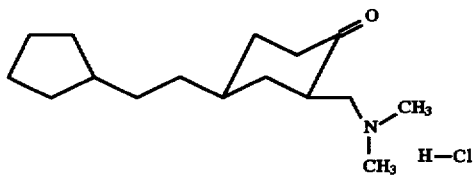

4-(2-cyclopentyl-ethyl)-2-dimethylaminomethyl-cyclohexanone hydrochloride (56)

Compound (55) was reacted with dimethylamine hydrochloride corresponding to the conditions described in Example 26, step 3. Compound (56) was obtained in a yield of 76% theoretical.

melting point: 127° C.–128° C.

5th step (1RS,2RS,4SR)-4-(cyclopentyl-ethyl)-2-dimethylaminomethyl-1-(3-methoxyphenyl)-cyclohexanol hydrochloride (52)

The base of compound (56) was reacted with 1-bromo-3-methoxy-benzene corresponding to the conditions described in Example 1. The base obtained was purified with diisopropyl ether via a silica gel column and was taken up in ether. After adding trimethylchlorosilane/water, compound (52) was obtained in a yield of 54% theoretical.

melting point: 154° C.–156° C.

Example 30

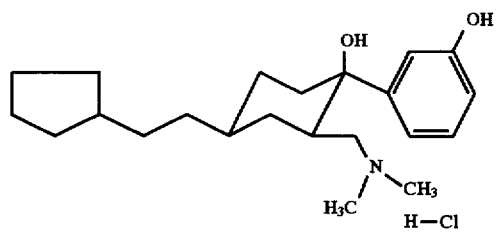

(1RS,2RS,4SR)-3-[4-(2-cyclopentyl-ethyl)-2-dimethylaminomethyl-1-hydroxy-cyclohexyl]-phenol hydrochloride (57)

The reaction was conducted in a nitrogen atmosphere with the exclusion of moisture. 1.44 g (4 mmole) of the base of compound (52) were dissolved in 15 ml toluene. 25 ml of 20% diisobutylaluminium hydride in toluene (35 mmole) were added drop-wise with stirring. The mixture was subsequently boiled for 6.5 hours under reflux and was cooled. 5 ml ethanol, followed by 5 ml of 1:1 ethanol/water and 35 ml toluene, were added drop-wise at a temperature between 0° C. and 10° C. After stirring for one hour, the salts obtained were filtered off by suction and the solvent was removed by distillation. The oil obtained was then taken up in ethyl acetate. After adding trimethylchlorosilane/water, compound (57) was obtained in a yield of 0.35 g (23% theoretical).

melting point: 226° C.–228° C.

Example 31

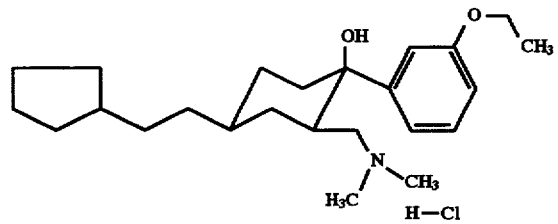

(1RS,2RS,4SR)-4-(cyclopentylethyl)-2-dimethylaminomethyl-1-(3-ethoxyphenyl)-cyclohexanol hydrochloride (58)

The base of compound (56) was reacted with 1-bromo-3-ethoxy-benzene corresponding to the conditions described in Example 1. The base obtained was purified with diisopropyl ether via a silica gel column and was taken up in 2-butanone/ether. After adding trimethylchlorosilane/water, compound (58) was obtained in a yield of 52% theoretical.

melting point: 152° C.–152.5° C.

Example 32

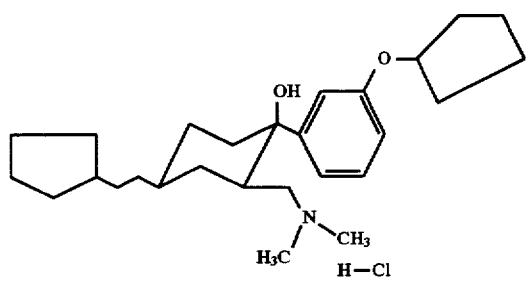

(1RS,2RS,4SR)-4-(2-cyclopentyl-ethyl-1-(3-
cyclopentyloxy-phenyl)-2-dimethylaminomethyl-
cyclohexanol hydrochloride (59)

The base of compound (56) was reacted with 1-bromo-3-cyclopentyloxy-benzene corresponding to the conditions described in Example 1. The base obtained was purified with diisopropyl ether via a silica gel column and was taken up in ethyl acetate/diisopropyl ether. After adding trimethylchlorosilane/water, compound (59) was obtained in a yield of 67% theoretical.

melting point: 140° C.–143° C.

Example 33

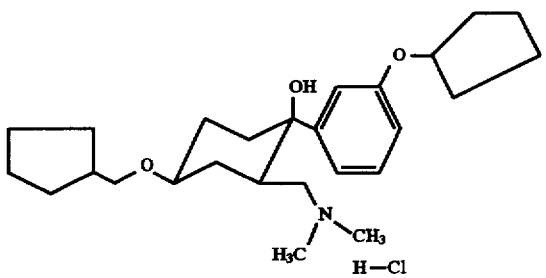

(1RS,2RS,4SR)-4-cyclopentylmethoxy-1-(3-
cyclopentyl-oxy-phenyl)-2-dimethylaminomethyl-
cyclohexanol hydrochloride (60)

1st step 4-(cyclopentylmethyloxy)-cyclohexanone (61)

23.7 g (150 mmole) 1,4-dioxa-spiro[4.5]decan-8-ol were dissolved in 120 ml dimethylformamide and stirred for 1 hour in a nitrogen atmosphere at room temperature with 7.2 g (159 mmole) of 50% sodium hydride in mineral oil. 38 g (150 mmole) toluene-4-sulphonic acid cyclopentylmethyl ester were then added (Krapcho, Johnson, J. Org. Chem., 36, 146, (1971). The mixture was stirred at room temperature and cooled to a temperature between 5° C. and 10° C. 125 ml water were then added dropwise. The product was extracted with ether and dried over sodium sulphate, and the solvent was removed by distillation. The product obtained (32 g) was dissolved in diisopropyl ether and stirred for 20 hours with 65 ml water and 95 ml concentrated hydrochloric acid. It was then neutralised with sodium hydrogen carbonate, extracted with ether and dried over sodium sulphate. The oil obtained (23.4 g) was purified with 1:1 diisopropyl ether/n-hexane via a silica gel column. 17.5 g of compound (61) were obtained (60% theoretical).

2nd step

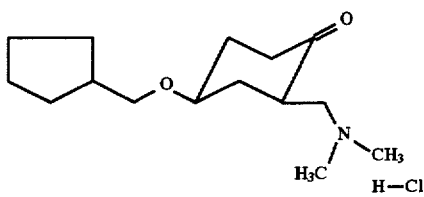

4-(cyclopentylmethyloxy)-2-dimethylaminomethyl-
cyclohexanone (62)

Compound (61) was reacted according to the conditions described in Example 26, step 3. Compound (62) was obtained in a yield of 90% theoretical.

3rd step (1RS,2RS,4SR)-4-cyclopentylmethoxy-1-(3-
cyclopentyl-oxy-phenyl)-2-dimethylaminomethyl-
cyclohexanol hydrochloride (60)

Compound (62) was reacted with 1-bromo-3-cyclopentyloxy-benzene corresponding to the conditions described in Example 1. A mixture of cis and trans isomers was formed, which was separated and purified with 20:1 ether/methanol via a silica gel column. The cis isomer was then taken up in 2-butanone and trimethylchlorosilane/water was added. After recrystallisation from 2-butanone, compound (60) was obtained in a yield of 12% theoretical.

melting point: 181° C.–182.5° C.

Example 34

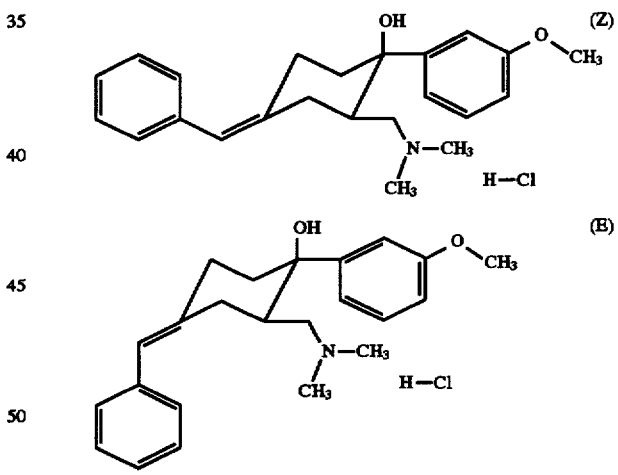

(E)-(1RS,2RS)-4-benzylidene-2-
dimethylaminomethyl-1-(3-methoxy-phenyl)-
cyclohexanol hydrochloride [E(63)]

and (Z)-(1RS,2RS)-4-benzylidene-2-
dimethylaminomethyl-1-(3-methoxy-phenyl)-
cyclohexanol hydrochloride [Z(63)]

1st step 7-dimethylaminomethyl-1,4-dioxa-spiro[4.5]decan-
8-one hydrochloride (64)

130 g (0.83 mole) 1,4-dioxa-spiro[4.5]-decan-8-one and 79.5 g (0.83 mole) dimethylammonium methylene chloride were stirred in 500 ml acetonitrile at room temperature. After adding 1 ml acetyl chloride, the mixture was stirred for 3 hours at room temperature, whereupon a clear, colourless solution was formed. 1 litre ether was then added drop-wise to the reaction mixture. 203 g (98% theoretical) 7-dimethylaminomethyl-1,4-dioxa-spiro[4.5]decan-8-one hydrochloride (64) were obtained in crystalline form.

2nd step

7-dimethylalaminomethyl-8-(3-methoxy-phenyl)-1,4-dioxa-spiro[4.5]decan-8-ol (65)

85 ml (0.68 mole) 1-bromo-3-methoxy-benzene, dissolved in 350 ml tetrahydrofuran, were added drop-wise to 16.4 g (0.68 mole) magnesium turnings in 50 ml tetrahydrofuran. The mixture was boiled for one hour under reflux and was cooled to a temperature between 5° C. and 10° C. The base was released from 7-dimethylaminomethyl-1,4-dioxa-spiro[4.5]-decan-8-one hydrochloride (64) with dichloromethane/aqueous sodium hydroxide solution, and the dichloromethane was removed by distillation after drying the solution. 95 g (0.45 mole) of the base obtained were dissolved in 150 ml tetrahydrofuran and added to the Grignard solution. The mixture was allowed to stand overnight and was subsequently cooled to a temperature between 5° C. and 10° C. The Grignard solution was decomposed by the addition of 600 ml of 20% ammonium chloride solution. The product was diluted with 500 ml tetrahydrofuran, the organic phase was separated off, and the aqueous phase was extracted twice with ether. After drying over sodium sulphate and removing the solvent by distillation, the residue (156 g) was introduced on to a silica gel column and eluted with 4:1 n-hexane/diisopropyl ether and then with 1:1 ethyl acetate/methanol. 137 g (94% theoretical) of base (65) were obtained as a light yellow, viscous oil.

3rd step

3-dimethylaminomethyl-4-hydroxy-4-(3-methoxy-phenyl)-cyclohexanone (66)

78 g (0.24 mmole) 7-dimethylaminomethyl-8-(3-methoxy-phenyl)-1,4-dioxaspiro[4.5]decan-8-ol (65) were dissolved in a 500 ml tetrahydrofuran and cooled to a temperature between 0° C. and 5° C. 200 ml of aqueous hydrochloric acid (2:1 concentrated hydrochloric acid/water) were added over 30 minutes. The mixture was stirred for 12 hours at room temperature and was subsequently cooled to a temperature between 0° C. and 5° C. After adding 250 ml of concentrated aqueous sodium hydroxide solution the product was extracted three times with ether and dried over sodium sulphate. After removing the solvent by distillation, the residue (66 g) was introduced on to a silica gel column and eluted successively with diisopropyl ether, 1:1 diisopropyl ether/ether and 1:1 ethyl acetate/methanol. 36 g base (66) (48%% theoretical) were obtained as a light yellow, viscous oil.

4th step

(E)-(1RS,2RS)-4-benzylidene-2-dimethylaminomethyl-1-(3-methoxy-phenyl)-cyclohexanol hydrochloride [E(63)]

and

(Z)-(1RS,2RS)-4-benzylidene-2-dimethylaminomethyl-1-(3-methoxy-phenyl)-cyclohexanol hydrochloride [Z(63)]

16.45 g (72.1 mmole) benzyl-phosphonic acid diethyl ester were dissolved in 70 ml dimethylformamide and treated with 4.28 g (80 mmole) sodium methanolate whilst being cooled in an ice bath. After stirring for 30 minutes, 10 g (36 mmole) 3-dimethylaminomethyl-4-hydroxy-4-(3-methoxy-phenyl)-cyclohexanone (66), dissolved in 20 ml dimethylformamide, were added drop-wise whilst cooling the mixture in an ice bath. The mixture was then heated to room temperature and stirred for 24 hours at this temperature. It was decomposed by the drop-wise addition of a mixture of 45 ml water and 25 ml methanol whilst being cooled in an ice bath. After extraction three times with ether, the product was washed with water and dried over magnesium sulphate. The ether was subsequently removed by distillation and the residue (15.8 g) was introduced on to a silica gel column. Elution with 7:1 diisopropyl ether/methanol gave 4.9 g of the [Z(63)] compound and 3.8 g of the [E(63)] compound, from which the hydrochlorides were obtained with trimethylchlorosilane/water in 2-butanone.

[Z(63)]
yield: 5.0 g (35% theoretical)
m.p.: 191° C.–192° C.

[E(63)]
yield: 3.9 g (28% theoretical)
m.p.: 220° C.–221° C.

Example 35

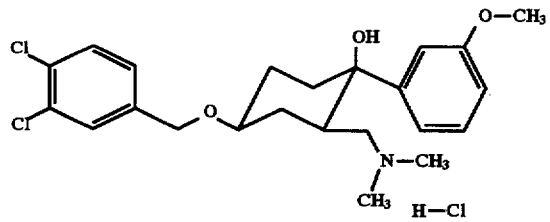

(1RS,2RS,4SR)-4-(3,4-dichloro-benzyloxy)-2-dimethyl-amino-methyl-1-(3-methoxy-phenyl)-cyclohexanol hydrochloride (67)

1st step

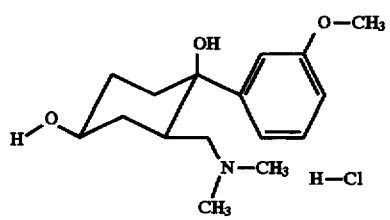

2-dimethylaminomethyl-1-(3-methoxy-phenyl)-cyclohexan-1,4-diol hydrochloride (68)

10 g (36 mmole) of compound (66) were dissolved in 80 ml isopropanol and cooled to 10° C. 0.56 g (15 mmole) sodium borohydride were added with stirring. The mixture was then stirred for two hours at room temperature. Whilst cooling the mixture in an ice bath, 20 ml dilute hydrochloric acid were added (1:4 conc. $HCl:H_2O$) followed by 10 ml of 20% aqueous sodium hydroxide solution. The product was extracted twice with dichloromethane. After drying and removal of the solvent by distillation, the crude product obtained (10.3 g) was dissolved in 2-butanone and was converted with trimethylchlorosilane/water into the hydrochloride for the separation of the diastereoisomers. 10.2 g (90% theoretical) of compound (68) crystallised out.

2nd step (1RS,2RS,4SR)-4-(3,4-dichloro-benzyloxy)-2-dimethyl-amino-methyl-1-(3-methoxy-phenyl)-cyclohexanol hydrochloride (67)

The base was released from compound (68) with dichloromethane/aqueous sodium hydroxide solution, and after drying the solution the dichloromethane was removed by distillation. 2.8 g (10 mmole) of the base obtained were dissolved in 10 ml dimethylformamide and treated with 480 mg sodium hydride (50%). The mixture was subsequently stirred for two hours at 55° C. 1.38 ml (1.95 g; 10 mmole) 1,2-dichloro-4-chloromethyl-benzene were added dropwise. After stirring for two hours at 55° C., the mixture was cooled to room temperature, poured on to ice/water, extracted three times with ether, washed with aqueous sodium hydroxide solution, and subsequently washed with water and dried over sodium sulphate. After removal of the solvent by distillation, 4.0 g of crude product were obtained and were introduced on to a silica gel column. Elution with 7:1 diisopropyl ether/methanol gave 3.0 g base, from which the compound of formula (67) (3.1 g; 65% theoretical), which had a melting point of 196° C.–197° C., was obtained with trimethylchlorosilane/water in 2-butanone.

Examples 36–61

Examples 36–61 are summarised in the following Tables. The compounds listed were prepared from the corresponding starting compounds under the conditions described in Examples 1–35.

| Ex. | Compound | X | $R^1$ | Y | $R^2$ | Melting point | $[\alpha]^{RT}_D$ | Prepared analogously to Ex. |
|---|---|---|---|---|---|---|---|---|
| 36 | (1RS, 2RS, 4SR)-3-(4-cyclopentylmethoxy)-2-dimethylamino-methyl-(1-hydroxy-cyclohexyl)-phenol hydrochloride (69) | O | H | O | cyclopentylmethyl | 188–191° C. | — | 6 |
| 37 | (−)-(1S, 2S, 4R)-4-(2-cyclopentylethyl)-1-(3-cyclopentyloxy-phenyl)-2-diphenylaminomethyl-cyclohexanol hydrochloride (70) | O | cyclopentyl | $CH_2$ | cyclopentylmethyl | 165.5–167° C. | −21° | 32 + 2 |
| 38 | (+)-(1R, 2R, 4S)-4-(2-cyclopentylethyl)-1-(3-cyclopentyloxy-phenyl)-2-diphenylaminomethyl-cyclohexanol hydrochloride (71) | O | cyclopentyl | $CH_2$ | cyclopentylmethyl | 193–194° C. | +22° | 32 + 2 |
| 39 | (−)-(1S, 2S, 4R)-4-(2-cyclopentylethyl)-2-diphenylaminomethyl-1-(3-methoxyphenyl)-cyclohexanol hydrochloride (72) | O | methyl | $CH_2$ | cyclopentylmethyl | 212–212.5° C. | −24° | 29 + 2 |
| 40 | (+)-(1R, 2R, 4S)-4-(cyclopentylethyl)-2-dimethylamino-methyl-1-(3-methoxyphenyl)-cyclohexanol hydrochloride (73) | O | methyl | $CH_2$ | cyclopentylmethyl | 211.5–212.5° C. | +27° | 29 + 2 |
| 41 | (−)-(1S, 2S, 4R)-4-(cyclopentylethyl)-2-dimethylamino-methyl-1-(3-ethoxyphenyl)-cyclohexanol hydrochloride (74) | O | ethyl | $CH_2$ | cyclopentylmethyl | 191–191.5° C. | −21° | 31 + 2 |
| 42 | (+)-(1R, 2R, 4S)-4-(cyclopentylethyl)-2-dimethylamino-methyl-1-(3-ethoxyphenyl)-cyclohexanol hydrochloride (75) | O | ethyl | $CH_2$ | cyclopentylmethyl | 191° C. | +26° | 31 + 2 |
| 43 | (−)-(1S, 2S, 4R)-4-benzyloxy-2-dimethylaminomethyl-1-[3-(2-fluoro-ethoxy)-phenyl]-cyclohexanol hydrochloride (76) | O | 2-fluoro-ethyl | O | benzyl | 161–163° C. | −17° | 3 + 2 |
| 44 | (+)-(1R, 2R, 4S)-4-benzyloxy-2-dimethylaminomethyl-1-[3-(2-fluoro-ethyoxy)-phenyl]-cyclohexanol hydrochloride (77) | O | 2-fluoro-ethyl | O | benzyl | 162–164° C. | +17° | 3 + 2 |
| 45 | (1RS, 2RS, 4SR)-2-dimethylaminomethyl-1-(3-methoxyphenyl)-4-propoxy-cyclohexanol hydrochloride (78) | O | methyl | O | n-propyl | 148–150° C. | — | 10 |
| 46 | (1RS, 2RS, 4SR)-4-(4-chloro-benzyloxy)-2-dimethylamino-methyl-1-(3-methoxyphenyl)-cyclohexanol hydrochloride (79) | O | methyl | O | 4-chloro-benzyl | 156° C. | — | 1 |
| 47 | (1RS, 2RS, 4SR)-2-dimethyl-aminomethyl-4-(4-fluoro-benzyl-oxy)-1-(3-methoxyphenyl)-cyclohexanol hydrochloride (80) | O | methyl | O | 4-fluoro-benzyl | 167° C. | — | 1 |
| 48 | (1RS, 2RS, 4SR)-2-dimethyl-aminomethyl-4-methoxy-1-(3-methoxy-phenyl)-cyclohexanol hydrochloride (81) | O | methyl | O | methyl | 188° C. | — | 10 |
| 49 | (1RS, 2RS, 4SR)-4-(4-tert-butyl-benzyloxy)-2-dimethylamino-methyl-1-(3-methoxyphenyl)-cyclohexanol hydrochloride (82) | O | $CH_3$ | O | 4-tert-butyl-benzyl | 189–190° C. | — | 1 |

-continued

| Ex. | Compound | X | R¹ | Y | R² | Melting point | $[\alpha]^{RT}_D$ | Prepared analogously to Ex. |
|---|---|---|---|---|---|---|---|---|
| 50 | (+)-(1R, 2R, 4S)-4-(4-benzyl-oxy)-2-dimethylaminomethyl-1-(3-isopropoxyphenyl)-cyclohexanol hydrochloride (83) | O | iso-propyl | O | benzyl | 167.5–170° C. | +20° | 4 + 2 |
| 51 | (–)-(1S, 2S, 4R)-4-benzyloxy-2-dimethylaminomethyl-1-(3-isopropoxyphenyl)-cyclohexanol hydrochloride (84) | O | iso-propyl | O | benzyl | 167–171° C. | –19.1° | 4 + 2 |
| 52 | (+)-(1R, 2R, 4S)-3-(4-benzyl-oxy-2-dimethylaminomethyl-1-hydroxycyclohexyl)-phenol hydrochloride (85) | O | H | O | benzyl | 199–202° C. | +21.2° | 6 + 2 |
| 53 | (–)-(1S, 2S, 4R)-3-(4-benzyl-oxy-2-dimethylaminomethyl-1-hydroxycyclohexyl)-phenol hydrochloride (86) | O | H | O | benzyl | 200–203° C. | –16.1° | 6 + 2 |
| 54 | (+)-(1R, 2R, 4S)-4-benzyloxy-1-(3-cyclopentyloxyphenyl)-2-dimethylaminomethyl-cyclohexanol hydrochloride (87) | O | cyclo-pentyl | O | benzyl | 115–129° C. | +18.6° | 32 + 2 |
| 55 | (–)-(1S, 2S, 4R)-4-benzyloxy-1-(3-cyclopentyloxyphenyl)-2-dimethylaminomethyl-cyclohexanol hydrochloride (88) | O | cyclo-pentyl | O | benzyl | 128–142° C. | –18.4° | 32 + 2 |
| 56 | (1RS, 2RS, 4SR)-3-[4-(4-chloro-benzyl-oxy)-2-dimethylamino-methyl-1-hydroxycyclohexyl]-phenol hydrochloride (89) | O | H | O | 4-chloro-benzyl | 242–246° C. | — | 6 |
| 57 | (–)-(1S, 2S, 4R)-2-dimethylamino-methyl-4-(4-fluoro-benzyl-oxy)-1-(3-methoxyphenyl)-cyclohexanol hydrochloride (90) | O | methyl | O | 4-fluoro-benzyl | 232–234° C. | –20.5° | 47 + 2 |
| 58 | (+)-(1R, 2R, 4S)-2-dimethyl-aminomethyl-4-(4-fluoro-benzyl-oxy)-1-(3-methoxyphenyl)-cyclohexanol hydrochloride (91) | O | methyl | O | 4-fluoro-benzyl | 232.5–234° C. | +20.3° | 47 + 2 |
| 59 | (–)-(1S, 2S, 4R)-4-(4-chloro-benzyloxy)-2-dimethylamino-methyl-1-(3-methoxyphenyl)-cyclohexanol hydrochloride (92) | O | methyl | O | 4-chloro-benzyl | 196.5–198° C. | –19.2° | 46 + 2 |
| 60 | (+)-(1R, 2R, 4S)-4-(4-chloro-benzyloxy)-2-dimethylamino-methyl-1-(3-methoxyphenyl)-cyclohexanol hydrochloride (93) | O | methyl | O | 4-chloro-benzyl | 196.5–197.5° C. | +20.7° | 46 + 2 |
| 61 | (1RS, 2RS, 4SR)-4-(4-chloro-benzyloxy)-2-dimethylamino-methyl-1-(3-isopropoxyphenyl)-cyclohexanol hydrochloride (94) | O | iso-propyl | O | 4-chloro-benzyl | 127–129° C. | — | 4 |

Pharmacological investigations
Testing for analgesia using the tail flick test on mice The analgesic effectiveness of the compounds according to the invention was investigated in the thermal radiation (tail flick) test on mice using the method of D'Amour and Smith (J. Pharm. Exp. Ther. 72, 74–79 (1941). Male NMRI mice with a weight between 20 and 24 g were used for this purpose. The animals were placed individually in special test cages and the bases of their tails were exposed to the focused thermal radiation from an electric lamp (Rhema Analgesi-emeter Type 3010). The lamp intensity was adjusted so that the time from switching on the lamp until the sudden twitching away of the tail (latency of pain) was 3–5 seconds for untreated animals. Before the administration of a compound according to the invention, the animals were pre-tested twice within five minutes and the average value of these measurements was calculated as the pre-test average.

The pain measurement was made 20, 40 and 60 minutes after intravenous administration. When the latency of pain increased, the maximum time of exposure was restricted to 12 seconds and an increase in the latent period to ≧150% of the pre-test average value was assessed as an analgesic effect. In order to determine the dosage-dependency, the respective compound according to the invention was applied in doses increasing logarithmically by a factor of 3–5, which included the threshold and the maximum effective dose each time. The $ED_{50}$ values were determined from the number of analgesic animals by the method of Litchfield and Wilcoxon (J. Pharm. Exp. Ther. 96, 99–1123, (1949)). Determination of the $ED_{50}$ was made at the effective maximum 20 minutes after intravenous administration of the substance.

All the compounds according to the invention which were used exhibited a pronounced analgesic effect. The results are summarised in the following Table.

TABLE

Testing for analgesia using the tail flick test on mice

| Example | Compound according to the invention | $ED_{50}$ (mg/kg intravenously) |
|---|---|---|
| 2 | [(+)1] | 0.049 |
| 2 | [(−)1] | 0.822 |
| 8 | [(+)6] | 0.190 |
| 11 | (14) | 0.379 |
| 22 | (35) | 2.430 |
| 33 | (60) | 2.460 |
| 38 | (71) | 3.350 |
| 52 | (85) | 0.068 |
| 60 | (93) | 0.370 |
| Tramadol | — | 14.700 |

What is claimed is:

1. A 1-phenyl-2-dimethylaminomethyl-cyclohexan-1-ol compound corresponding to formula I

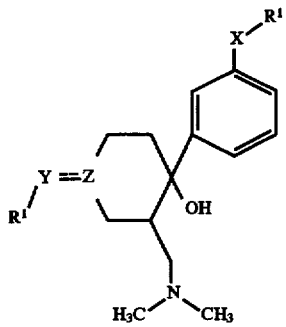

wherein

X represents O or S, $R^1$ represents H, $C_{1-6}$ alkyl, $C_{2-6}$ alkenyl, $C_{5-7}$ cycloalkyl, or halogenated $C_{1-6}$ alkyl, the grouping

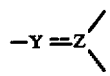

represents

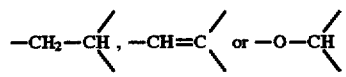

and $R^2$ represents $C_{1-6}$ alkyl, $C_{2-6}$ alkenyl, $C_{5-7}$ cycloalkylmethyl, substituted or unsubstituted phenyl, or substituted or unsubstituted benzyl, or a salt thereof with a physiologically acceptable acid.

2. A 1-phenyl-2-dimethylaminomethyl-cyclohexan-1-ol compound according to claim 1, wherein $R^1$ represents H, $C_{1-4}$ alkyl, 2'-methyl-2'-propenyl, cyclopentyl or fluoroethyl, with the proviso that $R^1$ is $C_{1-4}$ alkyl when X represents S, and $R^2$ represents $C_{1-4}$ alkyl, $C_{2-4}$ alkenyl, cyclopentylmethyl, phenyl, $C_{1-4}$ alkoxyphenyl, benzyl, $C_{1-4}$ alkylbenzyl, singly or doubly halogenated phenyl, or singly or doubly halogenated benzyl.

3. A 1-phenyl-2-dimethylaminomethyl-cyclohexan-1-ol compound according to claim 1, wherein $R^1$ represents H, methyl, ethyl, isopropyl, 2'-methyl-2'-propenyl, cyclopentyl or fluoroethyl, with the proviso that $R^1$ is methyl when X represents S, and $R^2$ represents methyl, propyl, 2'-methyl-propyl, allyl, 2'-methyl-2'-propenyl, cyclopentylmethyl, phenyl, 3-methoxyphenyl, benzyl, 4-tert-butylbenzyl, 4-chlorobenzyl, 4-fluorobenzyl or 3,4-dichlorobenzyl.

4. A 1-phenyl-2-dimethylaminomethyl-cyclohexan-1-ol compound according to claim 1, wherein $R^1$ represents H, methyl or cyclopentyl, with the proviso that $R^1$ is methyl when X represents S, the grouping

represents

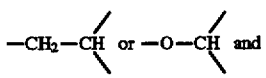

$R^2$ represents cyclopentylmethyl, benzyl or 4-chlorophenyl.

5. A 1-phenyl-2-dimethylaminomethyl-cyclohexan-1-ol compound according to claim 4, wherein X represents O, $R^1$ represents H or methyl, and $R^2$ represents benzyl.

6. A 1-phenyl-2-dimethylaminomethyl-cyclohexan-1-ol compound according to claim 1, wherein said compound has the configuration of formula Ia

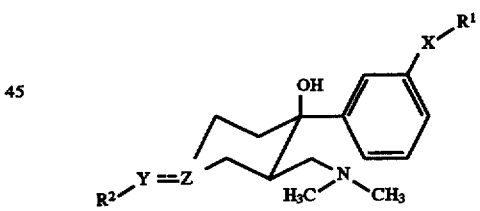

7. A pharmaceutical composition comprising an effective pain relieving amount of a 1-phenyl-2-dimethylaminomethyl-cyclohexan-1-ol compound according to claim 1, and at least one pharmaceutical carrier or adjuvant.

8. A method of relieving pain comprising administering to a patient in need of pain relief an effective pain relieving amount of a 1-phenyl-2-dimethylaminomethyl-cyclohexan-1-ol compound according to claim 1.

* * * * *

UNITED STATES PATENT AND TRADEMARK OFFICE
CERTIFICATE OF CORRECTION

PATENT NO. : 5,801,201  
DATED : September 1, 1998  
INVENTOR(S) : Ivars Graudums et al.

Page 1 of 1

It is certified that error appears in the above-identified patent and that said Letters Patent is hereby corrected as shown below:

<u>Column 2, lines 10-23, and column 45, lines 20-34,</u>  
Formula I should appear as follows:

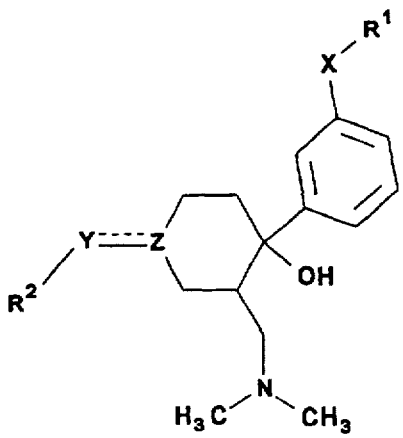

Signed and Sealed this

Twenty-second Day of January, 2002

Attest:

JAMES E. ROGAN  
Attesting Officer     Director of the United States Patent and Trademark Office